United States Patent [19]

MacFarlane et al.

[11] Patent Number: 5,671,735
[45] Date of Patent: Sep. 30, 1997

[54] METHOD AND APPARATUS FOR DETECTING AND MEASURING CONDITIONS AFFECTING COLOR

[75] Inventors: Darby Simpson MacFarlane; David Kenneth MacFarlane, both of Hastings-on-Hudson; Fred W. Billmeyer, Jr., Schenectady, all of N.Y.

[73] Assignee: Chromatics Color Sciences International, Inc., New York, N.Y.

[21] Appl. No.: 239,733

[22] Filed: May 9, 1994

Related U.S. Application Data

[63] Continuation-in-part of Ser. No. 21,657, Feb. 22, 1993, Pat. No. 5,313,267, which is a continuation of Ser. No. 818,488, Dec. 30, 1991, abandoned, which is a continuation of Ser. No. 402,815, Aug. 24, 1989, abandoned, which is a continuation-in-part of Ser. No. 306,286, Feb. 2, 1989, abandoned, which is a continuation of Ser. No. 204,938, Jun. 6, 1988, abandoned, which is a continuation of Ser. No. 904,369, Sep. 8, 1986, abandoned, which is a continuation-in-part of Ser. No. 833,661, Feb. 21, 1986, abandoned, which is a continuation of Ser. No. 514,618, Jul. 18, 1983, abandoned.

[51] Int. Cl.$^6$ ..................... A61B 5/00
[52] U.S. Cl. .................. 128/633; 128/665; 356/405
[58] Field of Search .................. 128/630, 632, 128/633, 665; 356/405

[56] References Cited

U.S. PATENT DOCUMENTS

| | | |
|---|---|---|
| Re. 31,815 | 1/1985 | Alfano .................. 128/665 |
| 205,578 | 7/1878 | Rose et al. . |
| 1,582,122 | 4/1926 | Clapp . |
| 1,629,330 | 5/1927 | Adler . |
| 1,741,080 | 12/1929 | Stenz . |

(List continued on next page.)

FOREIGN PATENT DOCUMENTS 655221  5/1995  European Pat. Off. .

(List continued on next page.)

OTHER PUBLICATIONS

M. Kenny et al. "Transcutaneous Bilirubin Monitoring of Newborns", *Annals of the New York Academy of Sciences*, vol. 428, pp. 251–262 (1984).

(List continued on next page.)

*Primary Examiner*—Jennifer Bahr
*Assistant Examiner*—Eric F. Winakur
*Attorney, Agent, or Firm*—Brumbaugh, Graves, Donohue & Raymond

[57] ABSTRACT

A method and apparatus for determining the condition of a test subject based on color uses a color measuring instrument to detect change in a color factor indicative of a condition such as a disease, spoilage, ageing, etc. A medical condition such as hyperbilirubinemia that affects skin color can be detected. One measures color factors such as Hunter b and L in the subjects' skin color. For predetermined ranges of one color factor, in particular L, changes in the other color factor, e.g. Hunter b, above predetermined levels are indicative of the medical condition. In many cases, a single measurement of the color factors can be utilized as a warning of the likelihood of the medical or contaminated condition, if the ordinary range of the color factor is known for healthy individuals with skin coloration like that of the test subject. Even if there has been no baseline measurement and the test subject's color is such that a single reading of one or two color factors will not warn of the possible presence of the medical condition or contamination, sequential readings can indicate the presence or absence of the condition based upon changes in the measured color factor, or lack of changes. The color measuring techniques apply to a wide range of biological test subjects (e.g. hair, teeth, tissue, excretions, foods, soil, animals, plants).

74 Claims, 3 Drawing Sheets

U.S. PATENT DOCUMENTS

| | | | |
|---|---|---|---|
| 1,979,119 | 10/1934 | Radzinsky | 35/17 |
| 2,221,774 | 11/1940 | Bowser . | |
| 3,003,388 | 10/1961 | Hunter et al. | 356/405 |
| 3,533,399 | 10/1970 | Goldberg et al. . | |
| 3,736,064 | 5/1973 | Kent et al. | 356/195 |
| 4,029,085 | 6/1977 | DeWitt et al. | 128/633 |
| 4,093,991 | 6/1978 | Christie, Jr. et al. | 364/525 |
| 4,135,497 | 1/1979 | Meyers et al. | 128/2 H |
| 4,241,738 | 12/1980 | Lübbers et al. | 128/666 |
| 4,267,844 | 5/1981 | Yamanishi | 128/633 |
| 4,302,971 | 12/1981 | Luk | 73/356 |
| 4,357,106 | 11/1982 | Tschirren et al. | 356/44 |
| 4,423,736 | 1/1984 | DeWitt et al. | 128/633 |
| 4,479,499 | 10/1984 | Alfano et al. | 128/665 |
| 4,561,850 | 12/1985 | Fabbri et al. | 434/100 |
| 4,654,794 | 3/1987 | O'Brien | 364/413 |
| 4,681,546 | 7/1987 | Hart | 434/99 |
| 4,723,554 | 2/1988 | Oman et al. | 128/664 |
| 4,842,523 | 6/1989 | Bourdier et al. | 434/371 |
| 4,857,071 | 8/1989 | Anderson | 8/414 |
| 4,877,034 | 10/1989 | Atkins et al. | 128/664 |
| 4,894,547 | 1/1990 | Leffell et al. | 250/461.2 |
| 4,909,632 | 3/1990 | Macfarlane | 356/402 |
| 4,964,874 | 10/1990 | Saphakkul | 8/429 |
| 5,127,406 | 7/1992 | Yamaguchi | 128/633 |
| 5,161,553 | 11/1992 | Cohen et al. | 132/205 |
| 5,259,382 | 11/1993 | Kronberg | 128/633 |
| 5,311,293 | 5/1994 | Macfarlane et al. | 356/421 |
| 5,313,267 | 5/1994 | MacFarlane et al. | 356/405 |
| 5,337,745 | 8/1994 | Benaron et al. | 128/633 |
| 5,344,463 | 9/1994 | Chan et al. | 8/408 |
| 5,353,790 | 10/1994 | Jacques et al. | 128/633 |
| 5,387,977 | 2/1995 | Berg et al. | 356/407 |

FOREIGN PATENT DOCUMENTS

| | | |
|---|---|---|
| 1347400 | 11/1963 | France . |
| 1468339 | 12/1966 | France . |
| 2587181 | 3/1987 | France . |
| 1236984 | 3/1967 | Germany . |
| 3827457 | 6/1989 | Germany . |
| 0037896 | 8/1985 | Japan . |
| 0257328 | 12/1985 | Japan . |
| 8401665 | 12/1985 | Netherlands . |
| 2001595 | 10/1993 | U.S.S.R. . |

OTHER PUBLICATIONS

R.E. Hannemann et al., "Neonatal Serum Bilirubin from Skin Reflectance", *Pediatric Research*, vol. 12, pp. 207–210 (1978).

F. Billmeyer, Jr., "Quantifying Color Appearance Visually and Instrumentally", *Color Research and Applications*, vol. 13, pp. 140–145 (1988).

T. Hegyi, M.D., "Transcutaneous Bilirubinometry In The Newborn Infant: State of the Art", *Journal of Clinical Monitoring*, vol. 2, pp. 53–59 (1986).

R.E. Hanneman et al., "Evaluation of Minolta Bilirubin Meter as a Screening Device", *Pediatrics*, vol. 69, pp. 107–109 (1982).

D. Onks et al., "Effect of Melanin, Oxyhemoglobin and Bilirubin on Transcutaneous Bilirubinometry", *Acta. Peadiatrica*, vol. 82, pp. 19–21 (1993).

F.D. Ortega et al., "Bilirrubinometria Transcutanea: Correlacion del Area de Medida Con La Espectropometria y Colorimetria Por Diazorreaccion", Am. Exp. Pediarr., vol. 39, pp. 438–440 (1993).

R.E. Schumacher, "Noninvasive Measurement of Bilirubin in the Newborn", *Clinics in Perinatology*, vol. 17, pp. 417–435 (1990).

I. Yamanouchi et al., "Transcutaneous Bilirubinometry: Preliminary Studies of Noninvasive Transcutaneous Bilirubin Meters in the Okayama National Hospital", *Pediatrics*, vol. 65, pp. 195–202 (1980).

Advertisement for portable photometer by Photo Research in *Optica Spectra*, Nov., 1973.

D. Tudehope et al., "Non–invasive method of measuring bilirubin levels in newborn infants", *Medical Journal of Australia*, vol. 1, pp. 165–168 (1982).

C. Jackson, *Color Me Beautiful*, New York, Ballantine Books, Apr. 1981, pp. 25, 26, Color Palettes, 37–39, 41–59, 61–74, 143–147.

G. Pickney et al., *Your New Image Through Color & Line*, California Fashion Image/Crown Summit Books, Sep. 1981, pp. 1–3, 17, 21–29, 97–105, 111, 112, 120–127.

R. Evans, *An Introduction To Color*, Wiley, New York, 1948, pp. 26–27 and 87–90.

C.S. McCamy et al., *A Color–Rendition Chart*, J. Appl. Photogr. Eng. vol. 2, pp. 95–99 (1976).

C.A. Pearson, *Face Colour As A Sighn Of Tuberculosis*, Color Res. Appl. vol. 7, pp. 31–33, (1982).

P.A. Lovett et al., *Measurement of the Skin Color of Babies in Hospital*, Proc. of CIBS Lighting Conference, 1986, HMSO, London, 1986, pp. 140–154.

G. Wyszecki et al., *Color Science*, 2nd Edition (1982) Table of Contents, pp. 63–72.

F. Billmeyer & M. Saltzman, "Principles of Color Technology," 2nd ed., John Wiley & Sons, New York, N.Y. 1981 pp. 18–19, 59–61, 92.

1

METHOD AND APPARATUS FOR DETECTING AND MEASURING CONDITIONS AFFECTING COLOR

SPECIFICATION

This is a continuation-in-part of U.S. patent application Ser. No. 08/021,657, filed Feb. 22, 1993, now U.S. Pat. No. 5,313,267, incorporated herein by reference. Ser. No. 08/021,657 is a continuation of Ser. No. 818,488, filed Dec. 30, 1991, now abandoned, a continuation of Ser. No. 402,815, filed Aug. 24, 1989, now abandoned, a continuation-in-part of Ser. No. 306,286, filed Feb. 2, 1989, now abandoned, a continuation of Ser. No. 204,938, filed Jun. 6, 1988, now abandoned, a continuation of Ser. No. 904,369, filed Sep. 8, 1986, now abandoned, a continuation-in-part of U.S. patent application Ser. No. 833,661, filed Feb. 21, 1986, now abandoned, which is a continuation of U.S. patent application Ser. No. 514,618, filed Jul. 18, 1983, now abandoned.

BACKGROUND OF THE INVENTION

This invention relates to a method and apparatus for the detection and/or measurement of a condition that affects the color of a test subject, and more particularly to a process and instrument for measuring at least one color characteristic or factor of a biological test subject indicative of the condition of interest.

Visual observation of a subject for changes in coloration indicative of a particular condition has often occurred. The subject may be a person or animal being observed to determine the presence or absence of a medical condition. The color characteristics or a single color characteristic of other test subjects such as biopsy specimens or excretions have diagnostic value.

An individual person's skin color is often assessed by her or his doctor. Hypertension, tuberculosis, sclerosis of the liver, to name just a few, are examples of ailments with symptomatic skin color changes among at least a sizeable population segment. Hair color evaluation and dental coloration evaluation are valuable. These may bear on the health of the individual, or on the health of the individual's hair and teeth, or these may permit accurate cosmetic activities, for example, to counteract graying or to accurately match new dental work to existing teeth.

Likewise, the condition of plants and agricultural products is visually inspected for color as an indication of condition. Contamination of soil is likewise apparent from visual inspection. Such visual inspections are subjective. Measuring by instrument the color characteristics that are key to the visual inspection has the benefit of objectivity and consistency.

In the past, hyperbilirubinemia in newborns has been detected by visually observing an individual for jaundice or by routinely taking and testing a blood sample. Upon detection, hyperbilirubinemia has been treated by phototherapy. During the course of phototherapy, blood samples have been taken and tested at regular intervals until it was determined that the level of serum bilirubin had decreased to an acceptable level.

In infants, there is little blood available for use in the blood testing for hyperbilirubinemia. So much blood is drawn that transfusions are often necessary to replace the drawn blood. The newborn is thereby exposed to all of the risks that transfusions bring. Blood sampling and transfusions are, of course, painful to the newborn, and as with any invasive procedure, both present medical risks, such as for example, risk of infection. There is a need, therefore, for a reliable, noninvasive technique for detecting and measuring a skin color affecting medical condition such as hyperbilirubinemia.

This is one example of a wider need for procedures and instruments to objectively and consistently determine a color characteristic or factor indicative of the condition of a test subject or indicative of a particular ailment or condition. The methods and apparatus of this invention can be employed where previously visual inspection, of which examples are given above, have been carried out at least in part on the basis of observable color characteristics.

BRIEF SUMMARY OF THE INVENTION

According to this invention there is provided a method and apparatus for detecting and quantitatively measuring a condition affecting the color of a test subject. The method includes measuring at least one color characteristic of the subject.

In one exemplary procedure according to this invention at least one skin color characteristic is measured at least at first and second points in time and compared for change to test for hyperbilirubinemia. In the preferred procedure a second skin color characteristic is also measured on the basis of which the subject can be assigned to one of plural categories among which varying amounts of change in the first-mentioned skin color characteristic are indicative of the presence of a medical condition. The first characteristic is then observed for a change of measured value sufficient to indicate the medical condition for a subject in that category. Preferably, a base reading of at least the first color characteristic is first made at a time the subject is without characteristic skin color change indicative of the medical condition for which he or she is to be tested.

In the case of hyperbilirubinemia detection, the first skin color characteristic is Hunter b, which is a color factor dependent on the relative content, in a color, of two opponent colors, yellow and blue. Hunter b is a factor comprising a first function (Y) weighted in a first portion of the spectrum, the yellower portion, a second function (Z) weighted in a second portion of the spectrum, the bluer portion, and a weighting term $(1/Y^{1/2})$ that is a function of the lightness of a color and that decreases the value of the color factor as lightness increases. Y and Z are part of the three tristimulus values X, Y and Z known to the color scientist for the purpose of defining a color. They are measurable by commercially available instruments such as colorimeters.

In the case of testing newborns for hyperbilirubinemia, readings of Hunter b and the Hunter lightness measure L are made shortly after birth. These can provide the base reading since hyperbilirubinemia does not manifest itself immediately after birth. The first reading is made typically within preferably five hours, but as soon as possible after birth. Subsequent readings, are then made during the next few days. The subsequent readings of Hunter b are compared with the first, baseline reading of Hunter b to determine whether Hunter b has increased to an extent that indicates a degree of jaundice characteristic of hyperbilirubinemia for a person having the subject's particular skin lightness L. L is measured during each subsequent test to be sure that it remains close to the original reading. This gives a degree of confidence that the test procedures are being conducted appropriately.

In the event that the medical condition affecting skin color is detected in a procedure like that described above for hyperbilirubinemia, then the measuring of skin color characteristics continues at regular intervals until the symptomatic color characteristic abates sufficiently to indicate the individual's recovery from the medical condition. In the case of hyperbilirubinemia, phototherapy is administered once a sufficient change in Hunter b is observed to indicate the jaundice of hyperbilirubinemia. Throughout the course of phototherapy, then, the Hunter b and L characteristics are continually monitored until the jaundice has been eliminated. This is valuable in removing the newborn from under the phototherapy lamps, since there is the danger of damage to the newborn's eyes in the event eye protection is prematurely removed or accidentally dislodged.

The apparatus used in accordance with this invention includes a color measuring device such as a colorimeter and computational means for storing and comparing the characteristic or characteristics that are measured when testing for the medical condition. Where Hunter b is measured for the purpose of detecting hyperbilirubinemia, a colorimeter capable of calculating Hunter b and L can be used. This can be a commercially available colorimeter with this capability. The computational means preferably has sufficient memory to store one or more previous readings and should be programmed to compare previous and current readings to detect changes in Hunter b and L. Preferably the colorimeter and the computational means are integrated in a single instrument, but the commercial colorimeter can be utilized in cooperation with, for example, a personal computer, which stores and can compare Hunter b and L values from measurements taken at timed intervals. Likewise, the computational means, whether an integrated part of the instrument or a separate computer, can be used to store ranges of lightness L and the increases in Hunter b that, for the various lightness ranges, indicate an unacceptable increase in serum bilirubin.

Preferably, each skin color characteristic measurement used to assess the presence or absence of the condition for which testing is carried out is actually an average of multiple tests. For example, when newborns are tested for the jaundice that signals hyperbilirubinemia, multiple readings are made at multiple sites. Five or six of the readings from which Hunter b and L (and perhaps a third characteristic, Hunter a, as described below) are made at, for example, each of several locations which may include some or all of two forehead locations, at least one chest location, a cheek location and two back locations. At each site, the Hunter readings that have the highest and lowest values of b are discarded, then all of the readings of each Hunter characteristic are averaged. Subsequent readings are made in the same manner and compared. As used herein, the terms "Hunter a", "Hunter b" and "Hunter L" include such average values, but are not limited to just the values arrived at by the averaging technique unless expressly so-limited. The discarding and averaging is readily accomplished by the computational provisions of the test equipment. The averaging technique may improve the testing of other than skin color where the testing steps of this invention are used, for example in the evaluation of hair by color measurement.

In skin color testing, it is important to cleanse the site utilizing a cleansing agent that does not contribute any coloration. Likewise, when testing is carried out on test subjects other than an individual's skin, the test subject should be free of any color altering contaminant. In skin color testing, the site on the test subject should be dry, and in all cases the instrument should have the capability of being applied to the site in such a manner that ambient light does not enter the instrument.

When testing in the manner described above, it is preferred to test for a third characteristic, as well, and using historical experience, determine whether that third characteristic lies outside an expected range of values, taking into account the values measured for the first and second characteristics. When testing for hyperbilirubinemia in the above procedure, the third characteristic is Hunter a. If the third characteristic is observed to have a value outside the range of normal expectations this may be an indication of error in the test procedure, in which case one conducting the test would not want to rely on the test results.

Determination of the first and second skin color characteristics at just one point in time can indicate or strongly suggest a medical condition affecting skin color if the first characteristic measurement is observed to lie outside a range of values for that characteristic known by experience to be normal for a subject having the particular measured value of the second characteristic. For example, in many individuals hyperbilirubinemia is strongly suggested if Hunter b and L are measured and it is determined that, based on skin color categories previously observed, Hunter b is above any ordinary value for a subject with skin having the L value measured. Also, even if baseline readings of Hunter b and L (and preferably a) are not made, changes in the value of Hunter b can signal the presence of hyperbilirubinemia if measurements of the Hunter values are made at timed intervals in the foregoing fashion. Out of the ordinary increases in Hunter b, of for example two or more points, can be an indication of hyperbilirubinemia when the measured L value remains in a constant range from one measurement to the next. Similarly, large decreases in Hunter b, of for example two or more points, can be an indication of hyperbilirubinemia from which the infant is recovering, again if L remains relatively constant.

Significant testing has established the value of the foregoing techniques in detecting hyperbilirubinemia. The same techniques will indicate other jaundice-producing medical conditions in human and animal subjects. Hepatitis or liver disorders are examples of such medical conditions susceptible to diagnosis with the methods and apparatus of this invention.

Tuberculosis has been observed to affect skin color in dark skinned individuals such as many persons of African descent. Appropriate color measurement in accordance with this invention may provide a valuable diagnostic tool.

Biopsy specimens, body fluids, excretions, etc. are visually inspected for color. The techniques and instrumentation according to this invention can provide objectivity and consistency to such inspections.

The above and further advantages of this invention will be better understood with reference to the following detailed description of the preferred embodiment taken in combination with the attached drawings.

BRIEF DESCRIPTION OF THE DRAWINGS

In the Drawings:

FIG. 1a is a diagrammatic illustration of exemplary memory content in an instrument like that of FIG. 1.

DETAILED DESCRIPTION OF THE PREFERRED EMBODIMENT

Figure 1:
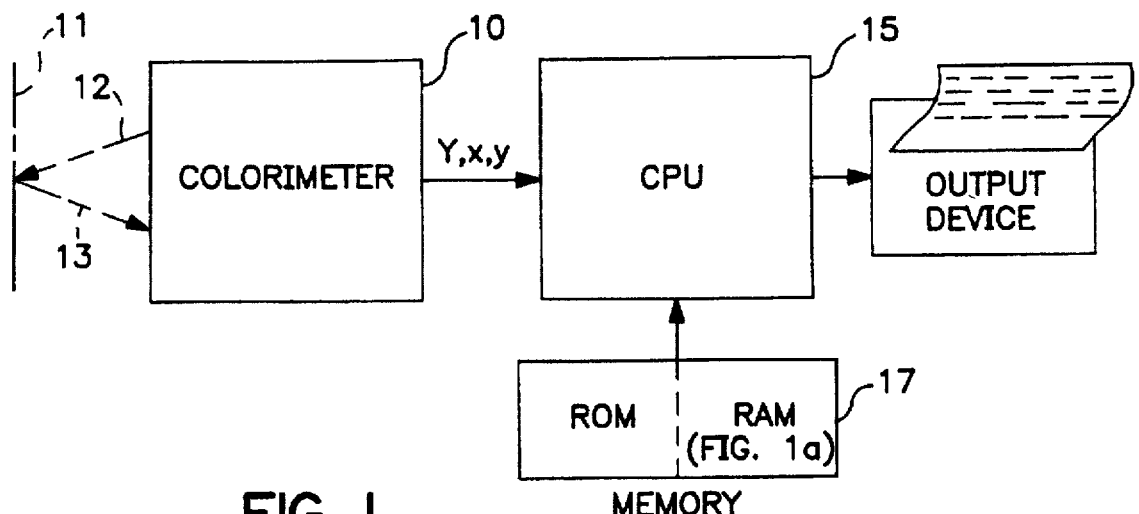
FIG. 1 is a block diagram illustration of an instrument for determining Hunter L, a and b values and for comparing changes in Hunter b to Hunter b changes predetermined to be indicative of bilirubinemia.

Any modern version of two general types of color-measuring instruments, colorimeters and spectrophotometers, is an example of instrument suitable for the skin color measurement according to a preferred embodiment of this invention. The basic components of either type of instrument are a light source, a sample illumination and viewing arrangement, a means of selecting certain wavelengths of light for the measurement, a detector of the light reflected from the sample, and some relatively simple computing capacity. In commercially available instruments the main purposes of the computing capacity are to store and apply calibration information and to calculate various color coordinates for later use. In FIG. 1, a color measuring instrument 10 is illustrated. An individual person's skin 11 is illuminated by the instrument as generally indicated by the broken line arrow 12 and the instrument receives illumination reflected from the skin 11 as generally indicated by the broken line arrow 13. Based on the illumination received by reflection from the skin, the instrument 10 develops the coordinates Y, x and y. In FIG. 1 the instrument 10 is a colorimeter, commercially available and suitable for development of the values Y, x and y.

Another type of instrument that can be used in the skin color categorization method according to this invention is the spectrophotometer that measures the skin reflectance at discrete wavelengths and from these data derives tristimulus values, from which can be computed the Hunter color values used to measure skin color for diagnostic purposes as discussed below.

Important to the use of a commercial colorimeter of the kind employed for the color measurement instrument 10 of FIG. 1 is the calibration of the instrument using a standard. In the early use of an instrument of this kind by the inventors, the "Light Skin" sample from the Macbeth Color Checker, described in the publication of C. S. McCamy, H. Marcus, and J. G. Davidson, "A Color-Rendition Chart," J. Appl. Photogr. Eng. 2, 95–99 (1976) was used. A tile of this approximate color was selected for its greater durability as an instrument standard. It was found, however, that the use of the "Light Skin" painted paper as the primary standard did not adequately avoid the phenomenon known as metamerism, by which objects that look alike (have the same perceived color) under some kinds of light sources or to some observers do not match under other types of light sources or to other observers. By this phenomenon colorimeters may not read their colors the same as the average human observer would under the daylight type light source usually employed for visual observation, hence leading to an error in colorimeter calibration.

As an improved primary standard, the skin of a subject whose skin color measurements were highly reproducible and in the approximate center of the range of skin colors of the human population was selected. The spectral reflectance factors of the skin of this subject were carefully measured on a Macbeth 1500 Plus spectrophotometer (Macbeth, New Windsor, N.Y.); these data are given in column 2 of Table I at the wavelengths listed in column 1. By using well-established techniques of computer color matching, carried out on an ACS 1800 system equipped with an ACS SpectroSensor II color measuring instrument (Datacolor International, Lawrenceville, N.J.) a colorant formulation matching this skin color was developed. The spectral reflectance factors for this match are given in column 3 of Table I. It may be seen that the data closely match those of column 2, indicating the absence of metamerism. Calculations according to the CIE 1976 CIELAB system showed that the two data sets match to within 0.27–0.36 units, less than can be perceived by human color vision, for daylight, incandescent light, and cool white fluorescent light, the three most commonly used light sources for the proposed applications.

The above-mentioned formulation was made up in a stable, durable material, and tiles were prepared as instrument standards. The spectral reflectance factors of one of these tiles are given in column 4 of Table I. It was found, however, that the improvement in calibration resulted in color coordinates that were significantly different from those obtained in the many studies made with the earlier system. A decision was made to adjust the calibration values of the new tiles in order to achieve consistent results between the new and old methods of calibration. Column 5 of Table I gives the adjusted set of spectral reflectance factors for the tile of column 4. The CIE and Hunter color coordinates, for measurement with the specular component excluded and calculated for CIE standard illuminant C and the 1931 2° CIE standard observer, are also tabulated for each of the samples in the table.

TABLE I

| Wavelengths, nm. | Skin Standard | Formulation | Tile, correct | Tile, adjusted |
|---|---|---|---|---|
| 400 | 19.03 | 20.70 | 21.51 | 16.67 |
| 420 | 18.96 | 20.69 | 21.10 | 16.93 |
| 440 | 21.53 | 21.68 | 20.99 | 17.65 |
| 460 | 25.36 | 24.43 | 23.27 | 20.56 |
| 480 | 28.06 | 28.30 | 27.82 | 25.67 |
| 500 | 30.13 | 30.77 | 29.03 | 27.94 |
| 520 | 31.19 | 31.31 | 29.38 | 28.24 |
| 540 | 30.01 | 30.84 | 28.48 | 27.59 |
| 560 | 31.41 | 30.76 | 28.22 | 27.33 |
| 580 | 32.85 | 34.01 | 31.49 | 30.12 |
| 600 | 44.37 | 43.54 | 42.58 | 40.52 |
| 620 | 51.24 | 51.57 | 51.27 | 47.93 |
| 640 | 54.56 | 55.09 | 55.56 | 51.10 |
| 660 | 57.09 | 57.60 | 59.22 | 53.82 |
| 680 | 58.67 | 60.41 | 61.82 | 56.55 |
| 700 | 59.95 | 62.69 | 63.93 | 58.87 |
| X | 37.14 | 37.28 | 36.14 | 33.76 |
| Y | 34.66 | 34.89 | 33.07 | 31.53 |
| Z | 28.50 | 28.54 | 27.63 | 24.20 |
| x | 0.3703 | 0.3702 | 0.3732 | 0.3732 |
| y | 0.3456 | 0.3464 | 0.3415 | 0.3523 |
| L | 58.87 | 59.07 | 57.51 | 56.15 |
| a | 9.31 | 9.02 | 11.54 | 9.05 |
| b | 12.51 | 12.70 | 11.77 | 13.75 |

With a suitable standard, basically, calibration is carried out by forcing the colorimeter 10 to give the desired color coordinates Y, x and y mentioned above, while utilizing the colorimeter with the standard tile chosen. The method of calibration is known for particular instruments and follows a series of steps prescribed by the manufacturer that need not be detailed here.

In skin color testing, prior to each test of a subject, each test site is cleansed. A cleansing agent such as isopropyl alcohol, which leaves behind no coloration, is suitable. The site is well dried to avoid any wetness which may interfere with the reflection of light from the skin 11 to the instrument 10. In all cases of testing, with the instrument correctly calibrated, the measuring head or instrument orifice is placed against the test site to be measured. Care is taken to avoid the admission of ambient light to the instrument. Pressing the head firmly against the test site prevents the entry of ambient light. Additionally, it was determined that best results are obtained if one removes the instrument from the test site briefly, between illuminations. This can be provided for in software by a conventional delaying routine and, if desired, with an appropriate display instructing the user to remove the instrument briefly well away from the skin.

In a colorimeter of the type shown in FIG. 1, at block 10 the instrument has an internal microprocessor or other computing capability so that it is able to develop the color coordinates Y, x and y from the measured values X, Y and Z (Y being the same in each case). Certain colorimeters develop the Hunter color coordinates L, a, and b. Since the degree of computation that the color measuring device 10 (i.e. colorimeter or spectrophotometer) internally performs varies, the manner of calculating the Hunter values from the tristimulus coordinates is useful to an understanding and practice of the invention and will enable correct use of a CPU by appropriate calculation to perform the invention with any commercially available colorimeter or spectrophotometer. Most modern color measuring instruments begin with measurement of the tristimulus vales X, Y, and Z. From these can be derived the CIE chromaticity coordinates x and y:

$$x=X/(X+Y+Z) \tag{1}$$

$$y=Y/(X+Y+Z) \tag{2}$$

The instrument 10 of FIG. 1 outputs the triplet of values x, y and Y as the starting point for further calculations by a central processing unit which can be dedicated microprocessor circuitry or personal computer 15. The remaining two tristimulus values X and Z are available by computation as follows:

$$X=xY/y, \tag{3}$$

and $$Z=(1-x-y)Y/y \tag{4}$$

In the preferred embodiment, in any event, the CPU according to FIG. 1 develops the Hunter value b discovered in accordance with this invention to be capable of use to detect and monitor hyperbilirubinemia. The Hunter b value is one of three values derived by Richard S. Hunter in 1958. Richard S. Hunter, "Photoelectric Color Difference Meter," J. Opt. Soc. Am. 48, 985–995 (1958). The equations for these are:

$$L=10 \, (Y)^{1/2} \tag{5}$$

$$a=17.5 \, (1.02 \, X-Y)/Y^{1/2} \tag{6}$$

$$b=7.0 \, (Y-0.847 \, Z)/Y^{1/2} \tag{7}$$

where L is a lightness coordinate whose values correlate better with the visual perceptions of the lightness of object colors than do values of Y; a is a coordinate denoting redness or greenness, for which positive values denote that the color is red rather than its opponent color green, and negative values denote the opposite; and b is a yellowness-blueness coordinate, for which positive values denote that the color is yellow rather than the opponent color blue, and negative values of b denote the opposite. For yellow colors, starting with a=b=0 and an appropriate high value of L, which would be a light grey, increasing positive values of b result in a series of colors that may be described as light yellowish grey, pale yellow, light yellow, brilliant yellow and vivid yellow, in turn. Thus b is a measure of the "intensity" of the yellow color.

Historically, all three Hunter values, a, b and L, have been utilized to describe a color. The inventors have determined that one can use the Hunter skin lightness measure L and comparative determinations of the Hunter value b developed at time intervals to measure the jaundice that is symptomatic of hyperbilirubinemia and by that measurement of jaundice detect the presence or absence of the ailment. The coordinate b provides a reliable measure of the yellow undertone of the color of human skin. In the particular arrangement of FIG. 1, wherein the colorimeter 10 produces the values Y, x, y, the computer 15 derives the Hunter values L and b. The Hunter lightness skin color characteristic L affects the amount of increase in the yellow measure Hunter b that indicates hyperbilirubinemia. Following the procedure represented in FIG. 2, steps 1 to 4 and preferably using an averaging technique described below, a newborn is measured, preferably within 2–5 hours of birth, to establish the initial, baseline values of Hunter L and b, $L_o$ and $b_o$. The values are recorded, step 4, for example by placement in machine memory 17. (A baseline Hunter a, $a_o$, may be calculated at this time, too, for the purposes explained below.) Thereafter, again preferably using the averaging technique, throughout the next several days, Hunter L and b are measured at intervals as represented by step 5 of FIG. 2. L is compared to the value originally measured as indicated at step 6. It should not vary more than 3 to 5 points, (depending on the range of L being measured) or the test is discontinued as at step 7. Otherwise, Hunter b is compared at step 8 to the baseline value established shortly after birth. As determined at step 9, if at any time Hunter b increases two points or more for darker skins with L values at or below approximately 51 or three points or more for lighter skins with L values above approximately 51, then hyperbilirubinemia is indicated and phototherapy, the usual treatment for this condition, may be prescribed. Alternatively, a blood test may be conducted to confirm the diagnosis before beginning phototherapy. Hunter b increases of one to two points for L values at or below approximately 51 and Hunter b increases of two to three points for L values above approximately 51 can be used as red flags or warning signs requiring closer monitoring.

When the measured value of Hunter L at any time is found to have varied more than 3–5 points the test procedure is suspect and the test may be discontinued. Hunter L variations of this magnitude do not ordinarily occur in skin color measurement. The test should be repeated and if the discrepancy is not eliminated then the comparison of Hunter b values should not be relied upon for a determination of the presence or absence of hyperbilirubinemia.

During phototherapy too, the testing procedure according to this invention can be used. Continued monitoring of Hunter L and b in the above manner can be utilized until Hunter b is within two points of its baseline value for subjects whose skin lightness value L is below a particular L value, or within three points of its baseline for subjects when L is above that value. An L value of approximately 51 has been found appropriate for this purpose.

Figure 3:
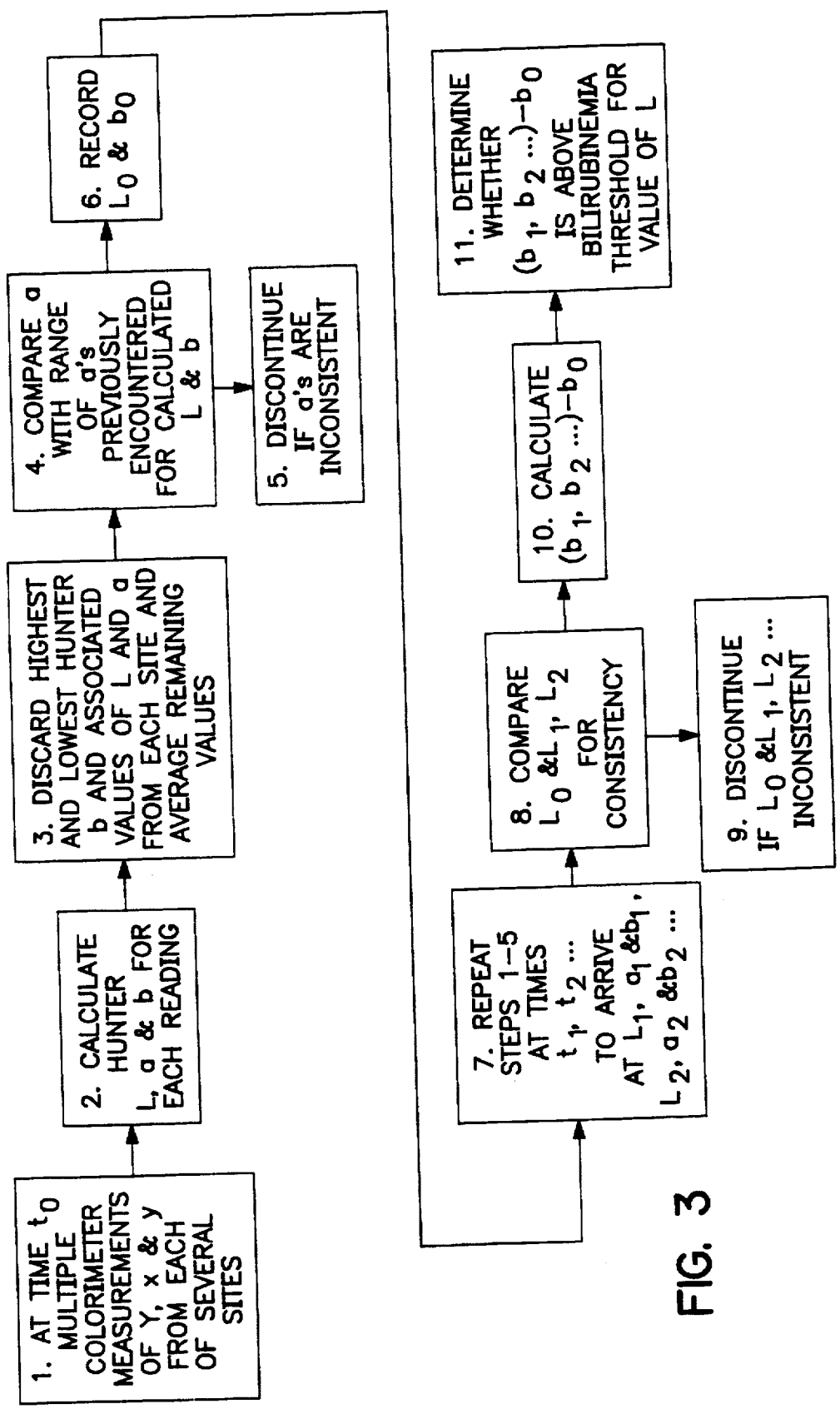
FIG. 3 is a schematic illustration in block diagram form illustrating the steps in the process of monitoring an infant for hyperbilirubinemia based on Hunter b including measuring and reviewing Hunter a as well as Hunter b and L.

Although it has not been found to affect the measurement of Hunter b or the reliability of the use of Hunter L and b to diagnose hyperbilirubinemia, it has been the inventors' practice to require measurement preferably of Hunter a at each testing. Again the averaging technique is preferably used as described below. Based upon the testing of the skin color of several million individuals, the inventors have identified some 210 broad categories of skin coloration. That is to say, 210 broad ranges of Hunter L, a and b have been identified. Hunter L and b values for each of these categories are shown in Table II, Appendix A hereto. Table III, below, provides the ranges of Hunter a reasonably to be expected. For certain values of L, Hunter a above a particular value has never been observed. Should the test indicate a Hunter a outside any previously observed range for a particular L and b, this would be taken as at least an indication of error in testing. This occurrence is represented at steps 4 and 5 of FIG. 3, which figure represents the steps in the hyperbilirubinemia test that includes the measurement and comparison of Hunter a. If retesting does not result in a value of Hunter a consistent with previous experience, then the use of Hunter L and b as a test for hyperbilirubinemia in this instance is discontinued.

TABLE III

| If Hunter L values are: | Then Hunter a values are: |
| --- | --- |
| 24 (or less) to 44 | 4 to 16 |
| 45 to 54 | 4 to 18 |
| 55 to 59 | 5 to 25 |
| 60 to 71 (or more) | 6 to 30 |

Figure 2:
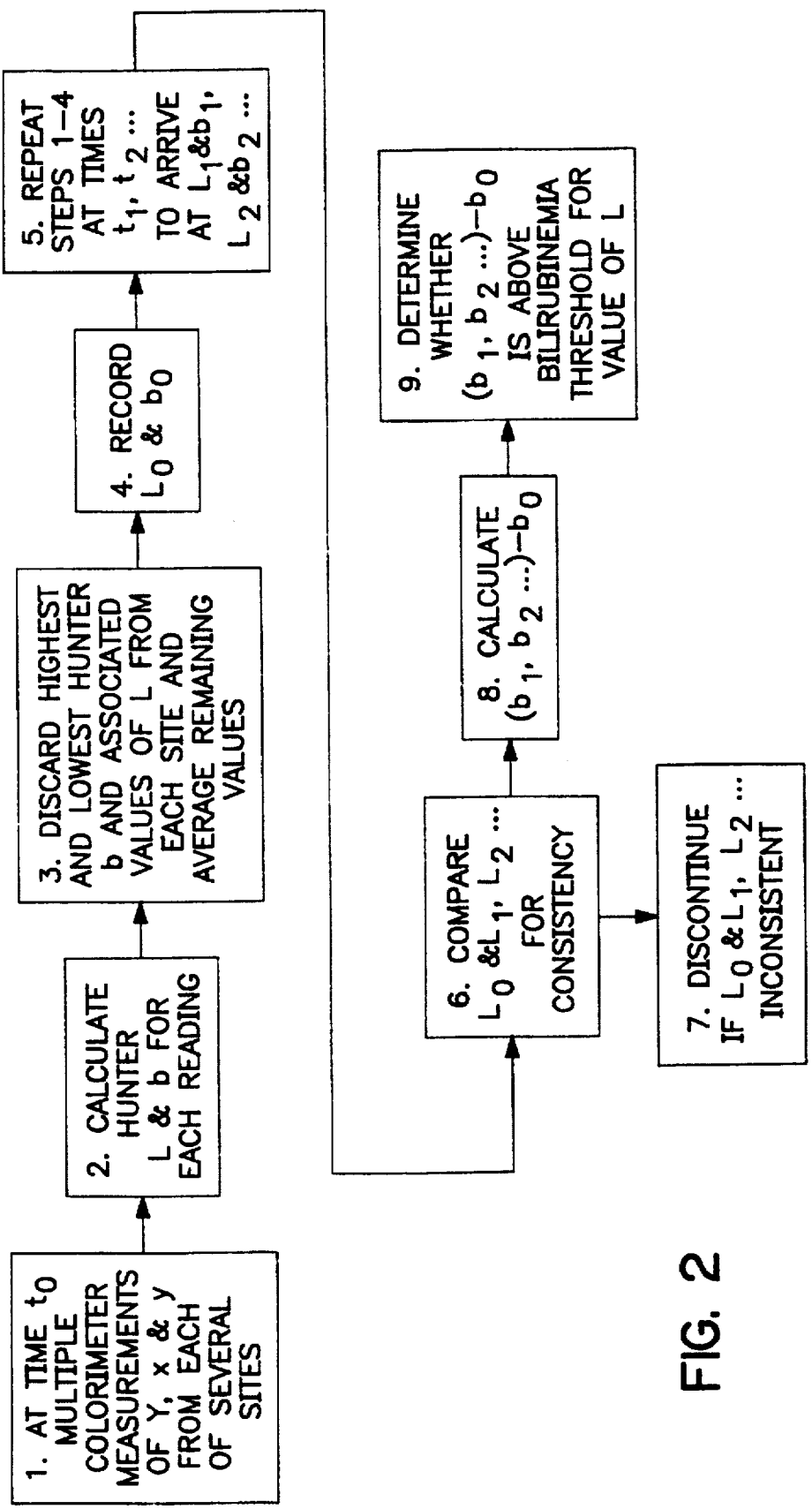
FIG. 2 is a schematic illustration in block diagram form illustrating the steps in the process of monitoring an infant for hyperbilirubinemia based upon changes in Hunter b in skin color and including measuring and reviewing Hunter b and L.

For greater accuracy, multiple Y, x and y readings are made with the colorimeter 10 at several different sites, for example at one or more locations on some or all of the subject's forehead, cheek, chest and back, as suggested in the steps of the method outlined in FIG. 2. In a preferred embodiment 5 or 6 readings at 5 different sites are made. Hunter b and L values are calculated for each reading. The high and low values of b and associated values of L from each site are discarded, the computer 15 then averages all of the remaining values of Hunter b and L. The average b and L thus calculated are then used as the Hunter b and L values in the previously described testing for bilirubinemia.

Some variation of b value occurs in dependence on the body location where readings are taken. Consistently averaging the values of L and b calculated from measurements taken at the same several locations on each individual can be used to eliminate any uncertainty resulting from such variations.

A hospital's measure of serum bilirubin typically uses a scale different from the measure of Hunter b detected by the above procedure. In extensive tests at one hospital, a linear relation was observed between serum bilirubin measured using the hospital's scale and the Hunter b measurement according to the invention. In that hospital 12 was the serum bilirubin value that signalled monitoring or treatment of hyperbilirubinemia.

Correlation between Hunter b and the hospital bilirubin count (BRC) was determined to be in accordance with the following equation:

$$BRC = 2.5 \left( [\{47/L\}^{1/2} b] - 6.8 \right) \quad (8)$$

where BRC equals the hospital bilirubin count, the number 47 is the average L for the entire database gathered over the course of research, and L and b are the average Hunter values determined as described above.

The term in braces modifies b according to the value L relative to its average, in this case 47, according to a square root (superscript ½) function. It may be easier to understand the above equation if it is written another way. If the modified b (in square brackets) is called MODB:

$$MODB = 6.8 + 0.4 \, BRC \quad (9)$$

The numbers 6.8 and 0.4 (=1/2.5) are, respectively, the intercept and slope of the straight line relation between modified b and BRC. The 6.8 is the value of MODB when BRC=0 and is related to the average baseline skin color. The 0.4 shows how rapidly MODB changes as BRC increases, an increase of 2.5 in BRC raises MODB by one point.

The equation is exemplary only and may vary in detail when applied to a larger database or to bilirubin count values from another hospital since hospitals do not have a standard scale used consistently from one hospital to the next. However, the linear relationship between MODB and BRC indicates relatively straightforward conversion of measured L and b to arrive at a particular hospital's bilirubin count value so that the medical practitioner can employ the optical measurement of jaundice in accordance with this invention in the same way she or he employed bilirubin count previously.

In the system of FIG. 1, following the routine of FIG. 2, from the initial measurement preferably within 2–5 hours of birth, the CPU calculates the initial Hunter values $L_0$, $a_0$ and $b_0$ and stores these in the Baseline Values addresses of the data portion or RAM of memory 17. The data RAM (or nonprogram) portion 18 of the memory 17 is indicated in FIG. 1a. A relatively permanent section 18a of RAM 18 stores the data of Table II (and Table III if Hunter a is to be checked) and data such as the ranges of L that establish categories of skin coloration for which varying Hunter b value changes are significant. A more often revised memory segment stores the results of the measurements performed with the instrument. Based on a relatively straightforward program retained in the permanent ROM memory, from the measurements taken at intervals, the CPU calculates the new values of L and b, retrieves $L_0$ and $b_0$, and subtracts those from the new values $L_1$ and $b_1$. The change in Hunter L and b, ΔL and Δb, can be displayed, or preferably, the CPU determines if the change in L indicates an error by comparing the change in L to that value, stored in the RAM 18 of the memory 17, that raises the suspicion of test error. If there is no suspicion of error, then the CPU determines whether an increase in b is above the value, again stored in memory, that indicates monitoring or treatment of hyperbilirubinemia for the particular value of L that has been measured. Similarly, for an infant that has previously been diagnosed with hyperbilirubinemia and is undergoing phototherapy, the same order of decrease to within 2 or 3 points of baseline, depending on L, can indicate recovery and phototherapy may be ended. The CPU memory 17 can be provided with Table II, or another compilation of the categories of skin coloration, which the CPU then can use as a look-up table to determine if Hunter a has a value outside of previously observed ranges for the particular Hunter L and b. Also, if desired, the CPU can calculate and display the hospital's measure of serum bilirubin based upon changes in Hunter b, for example by applying equation 8 above.

Even in the absence of an initial reading, based on observed ranges of skin coloration, measurement of Hunter L and b can warn of the likelihood of hyperbilirubinemia if a Hunter b value is measured that is in excess of Hunter b ordinarily observed for subjects with that value of L. Hunter b values exceeding those ordinarily observed for individuals in a particular range of Hunter L values can be determined by reference to Table II. For example, it will be apparent that no individual whose skin has a Hunter L value between 24 and 26 has measured above 13 in Hunter b. Such a measurement may be used to determine that a blood test is advisable. In all instances, however, even where there has not been a Hunter b baseline established, an increase over time of 2, 3 or more Hunter b points indicates the likelihood of hyperbilirubinemia, and if the change is a decrease, this is indicative of a recovering newborn.

Table IV is an actual set of measurements made on a three day old infant. Using the averaging technique described above, Hunter L of 48.0 and Hunter b of 11.1 is calculated. Converting to the hospital bilirubin count in the equation (9) above, a bilirubin count of 10.5 was calculated.

TABLE IV

|  | L | a | b | Y | x | y |
|---|---|---|---|---|---|---|
| Forehead | 47.8 | 21.6 | 11.6 | 22.9 | 0.411 | 0.333 |
|  | 48.6 | 19.5 | 11.5 | 23.6 | 0.404 | 0.335 |
|  | 48.8 | 21.2 | 11.6 | 23.8 | 0.407 | 0.333 |
|  | 46.7 | 21.6 | 11.6 | 21.8 | 0.413 | 0.333 |
|  | 48.6 | 21.6 | 11.8 | 23.6 | 0.410 | 0.333 |
|  | 48.0 | 22.1 | 11.7 | 23.1 | 0.412 | 0.332 |
| Forehead | 46.4 | 20.5 | 11.2 | 21.5 | 0.409 | 0.333 |
|  | 46.0 | 20.3 | 11.1 | 21.1 | 0.409 | 0.333 |
|  | 47.4 | 21.4 | 11.6 | 22.4 | 0.411 | 0.333 |
|  | 46.1 | 21.4 | 10.7 | 21.2 | 0.409 | 0.330 |
|  | 46.3 | 20.4 | 11.2 | 21.5 | 0.409 | 0.333 |
|  | 46.9 | 20.7 | 11.3 | 22.0 | 0.409 | 0.333 |
| Chest | 50.5 | 16.5 | 11.2 | 25.5 | 0.391 | 0.336 |
|  | 50.9 | 15.3 | 11.2 | 25.9 | 0.388 | 0.338 |
|  | 50.1 | 17.5 | 11.2 | 25.1 | 0.395 | 0.336 |
|  | 50.7 | 16.9 | 11.2 | 25.7 | 0.392 | 0.336 |
|  | 50.4 | 16.4 | 11.1 | 25.4 | 0.391 | 0.336 |
|  | 50.1 | 17.3 | 11.1 | 25.1 | 0.394 | 0.335 |
| Back | 49.0 | 17.1 | 11.1 | 24.0 | 0.395 | 0.336 |
|  | 48.7 | 16.3 | 11.0 | 23.7 | 0.394 | 0.337 |
|  | 48.3 | 16.6 | 10.6 | 23.3 | 0.393 | 0.335 |
|  | 49.2 | 16.6 | 10.9 | 24.2 | 0.393 | 0.336 |
|  | 49.1 | 18.3 | 11.3 | 24.1 | 0.399 | 0.335 |
|  | 50.0 | 18.0 | 11.4 | 25.0 | 0.397 | 0.336 |
| Back | 46.2 | 15.8 | 10.5 | 21.4 | 0.395 | 0.337 |
|  | 45.3 | 16.5 | 10.2 | 20.5 | 0.397 | 0.335 |
|  | 45.9 | 16.0 | 10.4 | 21.1 | 0.395 | 0.336 |
|  | 45.5 | 14.4 | 10.3 | 20.7 | 0.392 | 0.338 |
|  | 46.3 | 16.1 | 11.0 | 21.4 | 0.398 | 0.339 |
|  | 47.3 | 16.9 | 10.9 | 22.3 | 0.397 | 0.336 |

The invention can afford good evidence of jaundice resulting from medical conditions other than hyperbilirubinemia. Liver disorders in adults and children produce jaundice, for example. These and other skin color characteristics can be factors in diagnosing additional diseases that affect skin color. It has been observed, for example, that at least among dark skinned individuals, such as African Americans or others of African descent, skin color is affected by tuberculosis.

The application of the method and apparatus is not limited to the jaundice-related testing described above. Experiments with rhesus monkeys have shown a correlation between hormone levels and the coloration of the female monkey's very visible reddened hind end. An instrument like that described above was able to distinguish varying levels of reddening in an individual test subject's posterior using Hunter a and Hunter L in a similar fashion to that described above. The hormone level of the subject was thus indicated by the methods and apparatus of this invention.

Successful experimentation has begun on the evaluation of the condition of laboratory mice based upon the use of Hunter a and Hunter L in a similar fashion to that described above.

Table V, Appendix B, is a broad categorization of human hair coloration. Departure of an individual test subject's hair coloration from a baseline measure can be an indication of a change in the hair or of greying. In addition to diagnostic use, test procedures and instruments according to this invention can be used to determine how to restore the hair to its natural color, or with reference to the categories of Table V, hair that has changed in color by greying or by bleaching or dying can be restored to a more natural appearance, whether the test subject's original coloring or a chosen color consistent with the limitation of the categories identified in Table V.

In much the same way tooth coloration can be assessed by this invention and the techniques described can be used to arrive at a natural coloring of replacement dental work consistent with existing or replacement teeth.

Plant and crop specimens are good candidates for the application of the procedures and apparatus of the invention. For example, conditions leading to the degradation of grain stored in silos are observable based upon color change. Determination of these conditions by instrument is made possible by the techniques of the present invention, and this opens the way to automated monitoring for this purpose. Soil samples from oil spills when measured by these procedures and apparatus indicate the degree of soil contamination by oil or gasoline. Testing of such soil contamination has been successfully conducted. Biological test subjects of a great variety can be tested by means of the present invention. The color measuring techniques apply to a wide range of biological test subjects (e.g. hair, teeth, tissue, excretions, foods, soil, animals, plants).

From the foregoing it should be apparent that the methods and apparatus described are exemplary and not intended to limit the scope of protection of the invention as set forth in the appended claims.

TABLE II

APPENDIX A

| No. | Hunter L | Hunter b |
|---|---|---|
| 1. | <27 | −5* |
| 2. | <27 | 6 |
| 3. | <27 | 7 |
| 4. | <27 | 8 |
| 5. | <27 | 9 |
| 6. | <27 | 10 |
| 7. | <27 | 11 |
| 8. | <27 | 12+** |
| 9. | 27 to <30 | −5 |
| 10. | 27 to <30 | 6 |
| 11. | 27 to <30 | 7 |
| 12. | 27 to <30 | 8 |
| 13. | 27 to <30 | 9 |
| 14. | 27 to <30 | 10 |
| 15. | 27 to <30 | 11 |
| 16. | 27 to <30 | 12+ |
| 17. | 30 to <33 | −5 |
| 18. | 30 to <33 | 6 |
| 19. | 30 to <33 | 7 |
| 20. | 30 to <33 | 8 |
| 21. | 30 to <33 | 9 |
| 22. | 30 to <33 | 10 |
| 23. | 30 to <33 | 11 |
| 24. | 30 to <33 | 12+ |
| 25. | 33 to <36 | −5 |
| 26. | 33 to <36 | 6 |
| 27. | 33 to <36 | 7 |
| 28. | 33 to <36 | 8 |
| 29. | 33 to <36 | 9 |
| 30. | 33 to <36 | 10 |
| 31. | 33 to <36 | 11 |
| 32. | 33 to <36 | 12+ |
| 33. | 36 to <39 | −5 |

TABLE II-continued

APPENDIX A

| No. | Hunter L | Hunter b |
|---|---|---|
| 34. | 36 to <39 | 6 |
| 35. | 36 to <39 | 7 |
| 36. | 36 to <39 | 8 |
| 37. | 36 to <39 | 9 |
| 38. | 36 to <39 | 10 |
| 39. | 36 to <39 | 11 |
| 40. | 36 to <39 | 12 |
| 41. | 36 to <39 | 13 |
| 42. | 36 to <39 | 14 |
| 43. | 36 to <39 | 15+ |
| 44. | 39 to <42 | −5 |
| 45. | 39 to <42 | 6 |
| 46. | 39 to <42 | 7 |
| 47. | 39 to <42 | 8 |
| 48. | 39 to <42 | 9 |
| 49. | 39 to <42 | 10 |
| 50. | 39 to <42 | 11 |
| 51. | 39 to <42 | 12 |
| 52. | 39 to <42 | 13 |
| 53. | 39 to <42 | 14 |
| 54. | 39 to <42 | 15+ |
| 55. | 42 to <45 | −5 |
| 56. | 42 to <45 | 6 |
| 57. | 42 to <45 | 7 |
| 58. | 42 to <45 | 8 |
| 59. | 42 to <45 | 9 |
| 60. | 42 to <45 | 10 |
| 61. | 42 to <45 | 11 |
| 62. | 42 to <45 | 12 |
| 63. | 42 to <45 | 13 |
| 64. | 42 to <45 | 14 |
| 65. | 42 to <45 | 15 |
| 66. | 42 to <45 | 16 |
| 67. | 42 to <45 | 17 |
| 68. | 42 to <45 | 18+ |
| 69. | 45 to <48 | −5 |
| 70. | 45 to <48 | 6 |
| 71. | 45 to <48 | 7 |
| 72. | 45 to <48 | 8 |
| 73. | 45 to <48 | 9 |
| 74. | 45 to <48 | 10 |
| 75. | 45 to <48 | 11 |
| 76. | 45 to <48 | 12 |
| 77. | 45 to <48 | 13 |
| 78. | 45 to <48 | 14 |
| 79. | 45 to <48 | 15 |
| 80. | 45 to <48 | 16 |
| 81. | 45 to <48 | 17 |
| 82. | 45 to <48 | 18+ |
| 83. | 48 to <51 | −5 |
| 84. | 48 to <51 | 6 |
| 85. | 48 to <51 | 7 |
| 86. | 48 to <51 | 8 |
| 87. | 48 to <51 | 9 |
| 88. | 48 to <51 | 10 |
| 89. | 48 to <51 | 11 |
| 90. | 48 to <51 | 12 |
| 91. | 48 to <51 | 13 |
| 92. | 48 to <51 | 14 |
| 93. | 48 to <51 | 15 |
| 94. | 48 to <51 | 16 |
| 95. | 48 to <51 | 17 |
| 96. | 48 to <51 | 18 |
| 97. | 48 to <51 | 19 |
| 98. | 48 to <51 | 20+ |
| 99. | 51 to <54 | −5 |
| 100. | 51 to <54 | 6 |
| 101. | 51 to <54 | 7 |
| 102. | 51 to <54 | 8 |
| 103. | 51 to <54 | 9 |
| 104. | 51 to <54 | 10 |
| 105. | 51 to <54 | 11 |
| 106. | 51 to <54 | 12 |
| 107. | 51 to <54 | 13 |
| 108. | 51 to <54 | 14 |
| 109. | 51 to <54 | 15 |
| 110. | 51 to <54 | 16 |
| 111. | 51 to <54 | 17 |
| 112. | 51 to <54 | 18 |
| 113. | 51 to <54 | 19 |
| 114. | 51 to <54 | 20+ |
| 115. | 54 to <57 | −5 |
| 116. | 54 to <57 | 6 |
| 117. | 54 to <57 | 7 |
| 118. | 54 to <57 | 8 |
| 119. | 54 to <57 | 9 |
| 120. | 54 to <57 | 10 |
| 121. | 54 to <57 | 11 |
| 122. | 54 to <57 | 12 |
| 123. | 54 to <57 | 13 |
| 124. | 54 to <57 | 14 |
| 125. | 54 to <57 | 15 |
| 126. | 54 to <57 | 16 |
| 127. | 54 to <57 | 17 |
| 128. | 54 to <57 | 18 |
| 129. | 54 to <57 | 19 |
| 130. | 54 to <57 | 20+ |
| 131. | 57 to <60 | −5 |
| 132. | 57 to <60 | 6 |
| 133. | 57 to <60 | 7 |
| 134. | 57 to <60 | 8 |
| 135. | 57 to <60 | 9 |
| 136. | 57 to <60 | 10 |
| 137. | 57 to <60 | 11 |
| 138. | 57 to <60 | 12 |
| 139. | 57 to <60 | 13 |
| 140. | 57 to <60 | 14 |
| 141. | 57 to <60 | 15 |
| 142. | 57 to <60 | 16 |
| 143. | 57 to <60 | 17 |
| 144. | 57 to <60 | 18 |
| 145. | 57 to <60 | 19 |
| 146. | 57 to <60 | 20+ |
| 147. | 60 to <63 | −5 |
| 148. | 60 to <63 | 6 |
| 149. | 60 to <63 | 7 |
| 150. | 60 to <63 | 8 |
| 151. | 60 to <63 | 9 |
| 152. | 60 to <63 | 10 |
| 153. | 60 to <63 | 11 |
| 154. | 60 to <63 | 12 |
| 155. | 60 to <63 | 13 |
| 156. | 60 to <63 | 14 |
| 157. | 60 to <63 | 15 |
| 158. | 60 to <63 | 16 |
| 159. | 60 to <63 | 17 |
| 160. | 60 to <63 | 18 |
| 161. | 60 to <63 | 19 |
| 162. | 60 to <63 | 20+ |
| 163. | 63 to <66 | −5 |
| 164. | 63 to <66 | 6 |
| 165. | 63 to <66 | 7 |
| 166. | 63 to <66 | 8 |
| 167. | 63 to <66 | 9 |
| 168. | 63 to <66 | 10 |
| 169. | 63 to <66 | 11 |
| 170. | 63 to <66 | 12 |
| 171. | 63 to <66 | 13 |
| 172. | 63 to <66 | 14 |
| 173. | 63 to <66 | 15 |
| 174. | 63 to <66 | 16 |
| 175. | 63 to <66 | 17 |
| 176. | 63 to <66 | 18 |
| 177. | 63 to <66 | 19 |
| 178. | 63 to <66 | 20+ |
| 179. | 66 to <69 | −5 |
| 180. | 66 to <69 | 6 |
| 181. | 66 to <69 | 7 |
| 182. | 66 to <69 | 8 |
| 183. | 66 to <69 | 9 |

TABLE II-continued

APPENDIX A

| No. | Hunter L | Hunter b |
|---|---|---|
| 184. | 66 to <69 | 10 |
| 185. | 66 to <69 | 11 |
| 186. | 66 to <69 | 12 |
| 187. | 66 to <69 | 13 |
| 188. | 66 to <69 | 14 |
| 189. | 66 to <69 | 15 |
| 190. | 66 to <69 | 16 |
| 191. | 66 to <69 | 17 |
| 192. | 66 to <69 | 18 |
| 193. | 66 to <69 | 19 |
| 194. | 66 to <69 | 20+ |
| 195. | ≧69 | -5 |
| 196. | ≧69 | 6 |
| 197. | ≧69 | 7 |
| 198. | ≧69 | 8 |
| 199. | ≧69 | 9 |
| 200. | ≧69 | 10 |
| 201. | ≧69 | 11 |
| 202. | ≧69 | 12 |
| 203. | ≧69 | 13 |
| 204. | ≧69 | 14 |
| 205. | ≧69 | 15 |
| 206. | ≧69 | 16 |
| 207. | ≧69 | 17 |
| 208. | ≧69 | 18 |
| 209. | ≧69 | 19 |
| 210. | ≧69 | 20+ |

*The designation -5 means less than 5 but more than 4.
**The designation 12+ means more than 12 but less than 13.

TABLE V

APPENDIX B

| CATEGORY NAME | L Min | L Max | a Min | a Max | b Min | b Max |
|---|---|---|---|---|---|---|
| Black | 0.00 | 14.00 | -10.00 | 3.00 | -10.00 | 5.00 |
| Darkest Dark Brown | 14.00 | 16.00 | -10.00 | 3.00 | -10.00 | 1.00 |
| Darkest Dark Brown | 14.00 | 16.00 | -10.00 | 3.00 | 1.00 | 1.15 |
| Darkest Dark Brown | 14.00 | 16.00 | -10.00 | 3.00 | 1.15 | 1.25 |
| Darkest Dark Brown | 14.00 | 16.00 | -10.00 | 3.00 | 1.25 | 3.00 |
| Darker Dark Brown | 16.00 | 19.00 | -10.00 | 3.00 | -10.00 | 2.70 |
| Darker Dark Brown | 16.00 | 19.00 | -10.00 | 3.00 | 2.70 | 2.95 |
| Darker Dark Brown | 16.00 | 19.00 | -10.00 | 3.00 | 2.95 | 3.20 |
| Darker Dark Brown | 16.00 | 19.00 | -10.00 | 3.00 | 3.20 | 10.00 |
| Darker Dark Brown (Cool Auburn Tones) | 16.00 | 19.00 | 2.00 | 3.00 | -10.00 | 2.70 |
| Darker Dark Brown (Warm Auburn Tones) | 16.00 | 19.00 | 2.00 | 3.00 | 3.20 | 10.00 |
| Brown | 19.00 | 22.00 | 0.00 | 6.00 | -10.00 | 2.95 |
| Brown | 19.00 | 22.00 | 0.00 | 6.00 | 2.95 | 3.20 |
| Brown | 19.00 | 22.00 | 0.00 | 6.00 | 3.20 | 3.45 |
| Brown | 19.00 | 22.00 | 0.00 | 6.00 | 3.45 | 10.00 |
| Brown (Warm Auburn Tones) | 19.00 | 22.00 | 3.50 | 6.00 | 3.45 | 10.00 |
| Brown (Cool Auburn Tones) | 19.00 | 22.00 | 3.50 | 6.00 | -10.00 | 3.45 |
| Medium Brown | 22.00 | 27.00 | 1.00 | 6.00 | -10.00 | 3.75 |
| Medium Brown | 22.00 | 27.00 | 1.00 | 6.00 | 3.75 | 4.00 |
| Golden Med. Brown | 22.00 | 27.00 | 1.00 | 6.00 | 4.00 | 4.25 |
| Golden Med. Brown | 22.00 | 27.00 | 1.00 | 6.00 | 4.25 | 10.00 |
| Medium Brown (Warm Auburn Tones) | 22.00 | 27.00 | 3.50 | 6.00 | 4.25 | 10.00 |
| Medium Brown (Cool Auburn Tones) | 22.00 | 27.00 | 3.50 | 6.00 | -10.00 | 4.25 |
| Darkest Med. Blonde | 27.00 | 28.00 | 1.80 | 6.00 | -5.00 | 6.00 |
| Darkest Med. Blonde | 27.00 | 28.00 | 1.80 | 5.00 | 6.00 | 6.50 |
| Darkest Med. Blonde | 27.00 | 28.00 | 5.00 | 6.00 | 6.00 | 6.50 |
| Darkest Med. Blonde | 27.00 | 28.00 | 1.80 | 6.00 | 6.50 | 15.00 |
| Medium Blonde | 28.00 | 31.00 | 1.80 | 6.00 | -5.00 | 6.00 |
| Medium Blonde | 28.00 | 31.00 | 1.80 | 5.00 | 6.00 | 6.50 |
| Med. Golden Blonde | 28.00 | 31.00 | 5.00 | 6.00 | 6.00 | 6.50 |
| Med. Golden Blonde | 28.00 | 31.00 | 1.80 | 6.00 | 6.50 | 15.00 |
| Lightest Med. Blonde | 31.00 | 33.00 | 1.80 | 6.00 | -5.00 | 6.00 |
| Lightest Med. Blonde | 31.00 | 33.00 | 1.80 | 5.00 | 6.00 | 6.50 |
| Lightest Med. Blonde | 31.00 | 33.00 | 5.00 | 6.00 | 6.00 | 6.50 |
| Lightest Med. Blonde | 31.00 | 33.00 | 1.80 | 6.00 | 6.50 | 15.00 |
| Light Blonde | 33.00 | 36.00 | 1.80 | 6.00 | -5.00 | 7.00 |
| Light Blonde | 33.00 | 36.00 | 1.80 | 5.00 | 7.00 | 7.50 |
| Light Blonde | 33.00 | 36.00 | 5.00 | 6.00 | 7.00 | 7.50 |
| Light Blonde | 33.00 | 36.00 | 1.80 | 6.00 | 7.50 | 20.00 |
| Lighter Blonde | 36.00 | 40.00 | 1.80 | 6.00 | -5.00 | 8.00 |
| Lighter Blonde | 36.00 | 40.00 | 1.80 | 5.00 | 8.00 | 8.50 |
| Lighter Blonde | 36.00 | 40.00 | 5.00 | 6.00 | 8.00 | 8.50 |
| Lighter Blonde | 36.00 | 40.00 | 1.80 | 6.00 | 8.50 | 20.00 |
| Lightest Blonde | 40.00 | 80.00 | 1.80 | 7.00 | -5.00 | 9.00 |
| Lightest Blonde | 40.00 | 80.00 | 1.80 | 5.00 | 9.00 | 10.00 |
| Lightest Blonde | 40.00 | 80.00 | 5.00 | 7.00 | 9.00 | 10.00 |
| Lightest Blonde | 40.00 | 80.00 | 1.80 | 7.00 | 10.00 | 30.00 |
| Light Red | 22.00 | 28.00 | 6.00 | 30.00 | -5.00 | 3.50 |
| Light Red | 22.00 | 28.00 | 6.00 | 30.00 | 3.50 | 3.75 |
| Light Red | 22.00 | 28.00 | 6.00 | 30.00 | 3.75 | 4.00 |
| Light Red | 22.00 | 28.00 | 6.00 | 30.00 | 4.00 | 30.00 |
| Medium Red | 19.00 | 22.00 | 6.00 | 30.00 | -10.00 | 3.50 |
| Medium Red | 19.00 | 22.00 | 6.00 | 30.00 | 3.50 | 3.75 |
| Med. Golden Red | 19.00 | 22.00 | 6.00 | 30.00 | 3.75 | 4.00 |
| Med. Golden Red | 19.00 | 22.00 | 6.00 | 30.00 | 4.00 | 30.00 |
| Dark Red | 14.00 | 19.00 | 3.00 | 30.00 | -10.00 | 2.50 |
| Dark Red | 14.00 | 19.00 | 3.00 | 30.00 | 2.50 | 2.75 |
| Dark Red | 14.00 | 19.00 | 3.00 | 30.00 | 2.75 | 3.00 |
| Dark Red | 14.00 | 19.00 | 3.00 | 30.00 | 3.00 | 30.00 |
| Red Blonde | 27.00 | 40.00 | 6.00 | 30.00 | 6.00 | 30.00 |
| Red Blonde | 40.00 | 80.00 | 7.00 | 30.00 | 6.00 | 30.00 |
| Black/Dk Brown/Med Brown/Brown w/70%-90% Grey | 27.00 | 50.00 | -10.00 | 1.80 | -10.00 | 3.75 |
| Black/Dk Brown/Med Brown/Brown w/70%-90% Grey | 27.00 | 50.00 | -10.00 | 1.80 | 3.75 | 4.00 |
| Black/Dk Brown/Med Brown/Brown w/70%-90% Grey | 27.00 | 50.00 | -10.00 | 1.80 | 4.00 | 4.25 |
| Black/Dk Brown/Med Brown/Brown w/70%-90% Grey | 27.00 | 50.00 | -10.00 | 1.80 | 4.25 | 10.00 |
| Black/Dk Brown/Med Brown/Brown w/40%-60% Grey | 23.00 | 27.00 | -10.00 | 1.00 | -10.00 | 3.75 |

TABLE V-continued

APPENDIX B

| CATEGORY | L | | a | | b | |
|---|---|---|---|---|---|---|
| NAME | Min | Max | Min | Max | Min | Max |
| Black/Dk Brown/Med Brown/Brown w/40%–60% Grey | 23.00 | 27.00 | –10.00 | 1.00 | 3.75 | 4.00 |
| Black/Dk Brown/Med Brown/Brown w/40%–60% Grey | 23.00 | 27.00 | –10.00 | 1.00 | 4.00 | 4.25 |
| Black/Dk Brown/Med Brown/Brown w/40%–60% Grey | 23.00 | 27.00 | –10.00 | 1.00 | 4.25 | 10.00 |

Grey Hair

Light Brown/Darkest Blonde

| | | | | |
|---|---|---|---|---|
| 40%–60% Grey | 4.00 | 10.00 | –10.00 | –0.08 |
| 70%–90% Grey | 10.00 | to max | –10.00 | –0.08 |

Dark Red, Medium Red or Medium Light Red

| | | | | |
|---|---|---|---|---|
| 40%–60% Grey | 6.00 | 10.00 | –10.00 | –0.80 |
| 70%–90% Grey | 10.00 | to max | –10.00 | –0.80 |

Light Red or Red Blonde

| | | | | |
|---|---|---|---|---|
| 40%–60% Grey | 5.00 | 7.00 | –10.00 | –0.80 |
| 70%–90% Grey | 7.00 | to max | –10.00 | –0.80 |

Medium to Medium Dark Blonde

| | | | | |
|---|---|---|---|---|
| 40%–60% Grey | 1.70 | 4.00 | 0.00 | 0.00 |
| 70%–90% Grey | 4.00 | to max | 0.00 | 0.00 |

Light Blonde Hair

| | | | | |
|---|---|---|---|---|
| 40%–60% Grey | –99.99 | –0.25 | –1.75 | –1.25 |
| 70%–90% Grey | –99.99 | –0.25 | –99.99 | –1.75 |

*Negative values are used in this table in their ordinary sense, to denote values less than zero.

We claim:

1. A process of detecting a condition in a test subject, which condition includes a symptomatic, detectable change in the test subject's coloration, the process comprising the steps of:
   (a) at a first point in time, measuring with a color measuring instrument a value of at least one color factor in the test subject's coloration, said color factor being dependent, at least in part, on relative content of one or more colors in said coloration,
   (b) waiting an interval,
   (c) measuring with the color measuring instrument, at least at one further point in time, a value of said color factor in the test subject's coloration, and
   (d) comparing the values of said color factor measured at said first and said further point in time to determine whether there has been exhibited a change therein of a predetermined magnitude evidencing said condition, and
   wherein each of steps (a) and (c) comprises measuring the value of a color factor that is dependent on relative content of opponent colors in said coloration and on lightness of said coloration.

2. A process of detecting a condition in a test subject, which condition includes a symptomatic, detectable change in the test subject's coloration, the process comprising the steps of:
   (a) at a first point in time, measuring with a color measuring instrument a value of at least one color factor in the test subject's coloration, said color factor being dependent, at least in part, on relative content of one or more colors in said coloration,
   (b) waiting an interval,
   (c) measuring with the color measuring instrument, at least at one further point in time, a value of said color factor in the test subject's coloration, and
   (d) comparing the values of said color factor measured at said first and said further point in time to determine whether there has been exhibited a change therein of a predetermined magnitude evidencing said condition, and
   wherein each of steps (a) and (c) comprises measuring the value of a color factor that comprises a first function weighted in a first portion of the spectrum, a second function weighted in a second portion of the spectrum, and a weighting term that is a function of lightness of said coloration and that modifies the value of the color factor.

3. The process according to claim 2 wherein measuring the value of the color factor in each of steps (a) and (c) comprises measuring a factor that is a first function weighted in a yellower portion of the spectrum and a second function weighted in a bluer portion of the spectrum.

4. A process of detecting a condition in a test subject, which condition includes a symptomatic coloration; the process comprising the steps of:
   (a) measuring with a color measuring instrument a value in the test subject's coloration of at least one color factor, said color factor being dependent on said coloration and being correlatable, in test subjects having colorations of substantially varying degrees of lightness or darkness, to a measure of the condition that has clinical utility, and
   (b) comparing the measured value of said color factor with a predetermined range of values of the color factor to determine whether said measured value of said color factor evidences said condition in said test subject.

5. The process according to claim 4 wherein prior to step (b) the process further comprises the step of establishing the range of values of said color factor by recording values of Hunter b associated with at least one other color factor in individuals without said condition, and wherein step (b) comprises comparing a Hunter b value of the skin coloration of the test subject with the Hunter b values recorded for individuals comparable with the test subject in said other color factor of skin coloration.

6. The process according to claim 4 wherein
   step (b) comprises comparing the measured value of said color factor with a range of values of said color factor that is indicative of either the presence or absence of the condition in a subject to determine if the measured value of said color factor lies inside or outside the range.

7. The process according to claim 6 wherein step (a) comprises measuring the value of a color factor that is dependent on redness of the coloration of the test subject.

8. The process according to claim 4 wherein step (a) comprises measuring the value of color factor Hunter b, and the process further comprises measuring the value of said color factor in the coloration of the test subject subsequent to the first-mentioned measurement, determining any difference between the first-mentioned and subsequent measurements and comparing said difference to a range of values to determine whether a change in Hunter b value inside or outside said range is present, indicative of either the presence or absence of the condition.

9. A process of detecting a condition in a test subject, which condition includes a symptomatic, detectable change in the coloration of the test subject; the process comprising the steps of:

(a) at a first point in time, measuring with a color measuring instrument a value of relative content of opponent colors in the coloration of the test subject, (b) waiting an interval, (c) measuring with the color measuring instrument, at least at one further point in time, a value of relative content of said opponent colors in the coloration of the test subject, and (d) comparing the values measured at said first and said further points in time to determine whether there has been exhibited a change therein of a predetermined magnitude that evidences said condition and that is correlatable, in test subjects having colorations of substantially varying degrees of lightness or darkness, to a measure of said condition that has clinical utility.

10. The process according to claim 9 wherein each of steps (a) and (c) comprises measuring the value of a color factor that is dependent on lightness of the coloration of the test subject and that modifies the value of the relative content of the opponent colors in said coloration.

11. A process of detecting a condition in a test subject, which condition includes a symptomatic, detectable change in the test subject's coloration; the process comprising the steps of:

(a) at a first point in time, measuring with a color measuring instrument a value of at least one color factor in the test subject's coloration, said color factor being dependent, at least in part, on relative content of one or more colors in said coloration, (b) waiting an interval, (c) measuring with the color measuring instrument, at least at one further point in time, a value of said color factor in the test subject's coloration, (d) comparing the values of said color factor measured at said first and said further point in time to arrive at a value of change in color factor, and (e) comparing the value of change in color factor with a preestablished measure of color factor value change that is known to evidence said condition and that is correlatable, in test subjects having colorations of substantially varying degrees of lightness or darkness, to a measure of the condition that has clinical utility.

12. A process of detecting a condition in a test subject, which condition includes a symptomatic, detectable change in the test subject's coloration; the process comprising the steps of:

(a) at a first point in time, measuring with a color measuring instrument a value of at least one color factor Hunter b in the test subject's coloration, said color factor Hunter b being dependent, at least in part, on relative content of one or more colors in said coloration, (b) waiting an interval, (c) measuring with the color measuring instrument, at least at one further point in time, a value of said color factor Hunter b in the test subject's coloration, and (d) comparing the values of said color factor Hunter b measured at said first and further points in time to determine whether there has been exhibited a change therein of a predetermined magnitude evidencing said condition.

13. A process of detecting the jaundice caused by hyperbilirubinemia in an infant test subject, which jaundice includes a symptomatic, detectable change in the infant's coloration; the process comprising the steps of:

(a) establishing a baseline measurement for said infant by measuring with a color measuring instrument a value of at least one color factor in the infant's coloration at a first point in time following birth when jaundice resulting from hyperbilirubinemia is generally not present in an infant, said color factor being dependent, at least in part, on relative content of one or more colors in said coloration, (b) waiting an interval, (c) measuring with the color measuring instrument, at least at one further point in time, a value of said color factor in the infant's coloration, and (d) comparing the value of said color factor baseline measurement at said first point in time and said value of said color factor at the further point in time to determine whether there has been exhibited a change therein of a predetermined magnitude for that particular infant.

14. A process of detecting a condition in a test subject, which condition includes a symptomatic, detectable change in the test subject's coloration; the process comprising the steps of:

(a) establishing a plurality of coloration classes in which a predetermined magnitude of a change in value of at least one color factor is indicative of the condition, said predetermined magnitude indicative of the condition differing from one coloration class to another, (b) at a first point in time, measuring with a color measuring instrument a value of the at least one color factor in the test subject's coloration, said color factor being dependent, at least in part, on relative content of one or more colors in said coloration, (c) waiting an interval, (d) measuring with the color instrument, at east at one further point in time, a value of said color factor in the test subject's coloration, and (e) comparing the values of said color factor measured at said first and said further points in time to determine whether there has been exhibited a change therein of the predetermined magnitude evidencing said condition for the particular coloration class of the test subject.

15. The process according to claim 14 wherein the step of establishing a plurality of coloration classes comprises establishing a plurality of coloration classes that are colorations within varying ranges of lightness.

16. The process according to claim 15 wherein the color factor is Hunter b and the coloration classes are defined by ranges of values of Hunter L, the process further comprising the step of measuring by instrument a Hunter L value of the test subject's coloration.

17. The process according to claim 16 wherein the coloration is skin coloration and the step of establishing a plurality of coloration classes comprises establishing coloration classes that include a first class of skin coloration having a Hunter L value at or below substantially 51 and a second class of skin coloration having a Hunter L value above substantially 51, wherein increases in Hunter b values of substantially two or more points for skin coloration of the first class are indicative of hyperbilirubinemia, and wherein increases in Hunter b values of substantially three or more points for skin coloration of the second class are indicative of hyperbilirubinemia.

18. The process according to either claim 16, or 17 wherein said coloration classes are substantially as follows:

| No. | Hunter L | Hunter b |
|---|---|---|
| 1. | <27 | −5* |
| 2. | <27 | 6 |
| 3. | <27 | 7 |
| 4. | <27 | 8 |
| 5. | <27 | 9 |
| 6. | <27 | 10 |
| 7. | <27 | 11 |
| 8. | <27 | 12+** |
| 9. | 27 to <30 | −5 |
| 10. | 27 to <30 | 6 |
| 11. | 27 to <30 | 7 |
| 12. | 27 to <30 | 8 |
| 13. | 27 to <30 | 9 |
| 14. | 27 to <30 | 10 |
| 15. | 27 to <30 | 11 |
| 16. | 27 to <30 | 12+ |
| 17. | 30 to <33 | −5 |
| 18. | 30 to <33 | 6 |
| 19. | 30 to <33 | 7 |
| 20. | 30 to <33 | 8 |
| 21. | 30 to <33 | 9 |
| 22. | 30 to <33 | 10 |
| 23. | 30 to <33 | 11 |
| 24. | 30 to <33 | 12+ |
| 25. | 33 to <36 | −5 |
| 26. | 33 to <36 | 6 |
| 27. | 33 to <36 | 7 |
| 28. | 33 to <36 | 8 |
| 29. | 33 to <36 | 9 |
| 30. | 33 to <36 | 10 |
| 31. | 33 to <36 | 11 |
| 32. | 33 to <36 | 12+ |
| 33. | 36 to <39 | −5 |
| 34. | 36 to <39 | 6 |
| 35. | 36 to <39 | 7 |
| 36. | 36 to <39 | 8 |
| 37. | 36 to <39 | 9 |
| 38. | 36 to <39 | 10 |
| 39. | 36 to <39 | 11 |
| 40. | 36 to <39 | 12 |
| 41. | 36 to <39 | 13 |
| 42. | 36 to <39 | 14 |
| 43. | 36 to <39 | 15+ |
| 44. | 39 to <42 | −5 |
| 45. | 39 to <42 | 6 |
| 46. | 39 to <42 | 7 |
| 47. | 39 to <42 | 8 |
| 48. | 39 to <42 | 9 |
| 49. | 39 to <42 | 10 |
| 50. | 39 to <42 | 11 |
| 51. | 39 to <42 | 12 |
| 52. | 39 to −42 | 13 |
| 53. | 39 to <42 | 14 |
| 54. | 39 to <42 | 15+ |
| 55. | 42 to −45 | −5 |
| 56. | 42 to <45 | 6 |
| 57. | 42 to <45 | 7 |
| 58. | 42 to <45 | 8 |
| 59. | 42 to <45 | 9 |
| 60. | 42 to <45 | 10 |
| 61. | 42 to <45 | 11 |
| 62. | 42 to <45 | 12 |
| 63. | 42 to <45 | 13 |
| 64. | 42 to <45 | 14 |
| 65. | 42 to <45 | 15 |
| 66. | 42 to <45 | 16 |
| 67. | 42 to <45 | 17 |
| 68. | 42 to <45 | 18+ |
| 69. | 45 to <48 | −5 |
| 70. | 45 to <48 | 6 |
| 71. | 45 to <48 | 7 |
| 72. | 45 to <48 | 8 |
| 73. | 45 to <48 | 9 |
| 74. | 45 to <48 | 10 |
| 75. | 45 to <48 | 11 |

-continued

| No. | Hunter L | Hunter b |
|---|---|---|
| 76. | 45 to <48 | 12 |
| 77. | 45 to <48 | 13 |
| 78. | 45 to <48 | 14 |
| 79. | 45 to <48 | 15 |
| 80. | 45 to <48 | 16 |
| 81. | 45 to <48 | 17 |
| 82. | 45 to <48 | 18+ |
| 83. | 48 to <51 | −5 |
| 84. | 48 to <51 | 6 |
| 85. | 48 to <51 | 7 |
| 86. | 48 to <51 | 8 |
| 87. | 48 to <51 | 9 |
| 88. | 48 to <51 | 10 |
| 89. | 48 to <51 | 11 |
| 90. | 48 to <51 | 12 |
| 91. | 48 to <51 | 13 |
| 92. | 48 to <51 | 14 |
| 93. | 48 to <51 | 15 |
| 94. | 48 to <51 | 16 |
| 95. | 48 to <51 | 17 |
| 96. | 48 to <51 | 18 |
| 97. | 48 to <51 | 19 |
| 98. | 48 to <51 | 20+ |
| 99. | 51 to <54 | −5 |
| 100. | 51 to <54 | 6 |
| 101. | 51 to <54 | 7 |
| 102. | 51 to <54 | 8 |
| 103. | 51 to <54 | 9 |
| 104. | 51 to <54 | 10 |
| 105. | 51 to <54 | 11 |
| 106. | 51 to <54 | 12 |
| 107. | 51 to <54 | 13 |
| 108. | 51 to <54 | 14 |
| 109. | 51 to <54 | 15 |
| 110. | 51 to <54 | 16 |
| 111. | 51 to <54 | 17 |
| 112. | 51 to <54 | 18 |
| 113. | 51 to <54 | 19 |
| 114. | 51 to <54 | 20+ |
| 115. | 54 to <57 | −5 |
| 116. | 54 to <57 | 6 |
| 117. | 54 to <57 | 7 |
| 118. | 54 to <57 | 8 |
| 119. | 54 to <57 | 9 |
| 120. | 54 to <57 | 10 |
| 121. | 54 to <57 | 11 |
| 122. | 54 to <57 | 12 |
| 123. | 54 to <57 | 13 |
| 124. | 54 to <57 | 14 |
| 125. | 54 to <57 | 15 |
| 126. | 54 to <57 | 16 |
| 127. | 54 to <57 | 17 |
| 128. | 54 to <57 | 18 |
| 129. | 54 to <57 | 19 |
| 130. | 54 to <57 | 20+ |
| 131. | 57 to <60 | −5 |
| 132. | 57 to <60 | 6 |
| 133. | 57 to <60 | 7 |
| 134. | 57 to <60 | 8 |
| 135. | 57 to <60 | 9 |
| 136. | 57 to <60 | 10 |
| 137. | 57 to <60 | 11 |
| 138. | 57 to <60 | 12 |
| 139. | 57 to <60 | 13 |
| 140. | 57 to <60 | 14 |
| 141. | 57 to <60 | 15 |
| 142. | 57 to <60 | 16 |
| 143. | 57 to <60 | 17 |
| 144. | 57 to <60 | 18 |
| 145. | 57 to <60 | 19 |
| 146. | 57 to <60 | 20+ |
| 147. | 60 to <63 | −5 |
| 148. | 60 to <63 | 6 |
| 149. | 60 to <63 | 7 |
| 150. | 60 to <63 | 8 |
| 151. | 60 to <63 | 9 |
| 152. | 60 to <63 | 10 |
| 153. | 60 to <63 | 11 |

-continued

| No. | Hunter L | Hunter b |
|---|---|---|
| 154. | 60 to <63 | 12 |
| 155. | 60 to <63 | 13 |
| 156. | 60 to <63 | 14 |
| 157. | 60 to <63 | 15 |
| 158. | 60 to <63 | 16 |
| 159. | 60 to <63 | 17 |
| 160. | 60 to <63 | 18 |
| 161. | 60 to <63 | 19 |
| 162. | 60 to <63 | 20+ |
| 163. | 63 to <66 | −5 |
| 164. | 63 to <66 | 6 |
| 165. | 63 to <66 | 7 |
| 166. | 63 to <66 | 8 |
| 167. | 63 to <66 | 9 |
| 168. | 63 to <66 | 10 |
| 169. | 63 to <66 | 11 |
| 170. | 63 to <66 | 12 |
| 171. | 63 to <66 | 13 |
| 172. | 63 to <66 | 14 |
| 173. | 63 to <66 | 15 |
| 174. | 63 to <66 | 16 |
| 175. | 63 to <66 | 17 |
| 176. | 63 to <66 | 18 |
| 177. | 63 to <66 | 19 |
| 178. | 63 to <66 | 20+ |
| 179. | 66 to <69 | −5 |
| 180. | 66 to <69 | 6 |
| 181. | 66 to <69 | 7 |
| 182. | 66 to <69 | 8 |
| 183. | 66 to <69 | 9 |
| 184. | 66 to <69 | 10 |
| 185. | 66 to <69 | 11 |
| 186. | 66 to <69 | 12 |
| 187. | 66 to <69 | 13 |
| 188. | 66 to <69 | 14 |
| 189. | 66 to <69 | 15 |
| 190. | 66 to <69 | 16 |
| 191. | 66 to <69 | 17 |
| 192. | 66 to <69 | 18 |
| 193. | 66 to <69 | 19 |
| 194. | 66 to <69 | 20+ |
| 195. | ≥69 | −5 |
| 196. | ≥69 | 6 |
| 197. | ≥69 | 7 |
| 198. | ≥69 | 8 |
| 199. | ≥69 | 9 |
| 200. | ≥69 | 10 |
| 201. | ≥69 | 11 |
| 202. | ≥69 | 12 |
| 203. | ≥69 | 13 |
| 204. | ≥69 | 14 |
| 205. | ≥69 | 15 |
| 206. | ≥69 | 16 |
| 207. | ≥69 | 17 |
| 208. | ≥69 | 18 |
| 209. | ≥69 | 19 |
| 210. | ≥69 | 20+ | wherein −5 represents a value less than 5 but more than 4, and 12+, 15+, 18+, and 20+ represent a value more than 12, 15, 18, and 20, respectively, but less than 13, 16, 19, and 21, respectively.

19. The process according to either claim 15 or 14 wherein said coloration classes are determined by ranges of Hunter L values; said ranges of Hunter L values being bounded by at least one of the Hunter L values substantially as follows:

Hunter L=27, 30, 33, 36, 39, 42, 45, 48, 54, 57, 60, 63, 66 and 69.

20. The process according to claim 14 wherein each of steps (b) and (d) comprises measuring the value of said color factor at different locations on the test subject.

21. The process according to claim 14 wherein each of steps (b) and (d) comprises making a set of multiple measurements of the color factor value at each of the respective points in time and averaging each set of multiple measurements.

22. A process of detecting a medical condition, which condition includes a symptomatic, detectable change in a test subject's coloration; the process comprising the steps of:
 (a) establishing a baseline measurement for said test subject by measuring with a color measuring instrument a value of at least one color factor in the test subject's coloration at a first point in time when the symptomatic, detectable change in coloration resulting from the medical condition is generally not present in a test subject, said color factor being dependent, at least in part, on relative content of one or more colors in said coloration,
 (b) waiting an interval,
 (c) measuring with the color measuring instrument, at least at one further point in time, a value of said color factor in the test subject's coloration, and
 (d) comparing the value of said color factor baseline measurement at said first point in time and said value of said color factor at the further point in time to determine whether there has been exhibited a change therein of a predetermined magnitude for that particular test subject.

23. The process according to any one of claims 1, 13 or 22 wherein each of steps (a) and (c) comprises measuring the value of a color factor that comprises a first function weighted in a yellower portion of the spectrum and a second function weighted in a bluer portion of the spectrum.

24. The process according to any one of claims 1, 4, or 22 wherein step (a) comprises measuring the value of color factor Hunter a.

25. A process of detecting the condition of a test subject based on coloration of said test subject; the process comprising the steps of:
 (a) measuring with a color measuring instrument the value of at least one color factor Hunter b in said coloration of the test subject, and
 (b) comparing the measured value of said color factor Hunter b with a range of values of Hunter b that are indicative of either the presence or absence of the condition in a subject to determine if the measured value of said color factor lies inside or outside the range.

26. A process of detecting a condition in a test subject, which condition includes a symptomatic coloration; the process comprising the steps of:
 (a) measuring with a color measuring instrument a value of at least one color factor, Hunter b, in the test subject's coloration, said color factor being dependent on said coloration,
 (b) comparing the measured value of said color factor with a predetermined range of values of the color factor to determine whether said measured value of said color factor evidences said condition in said test subject,
 (c) measuring the value of said color factor in the coloration of the test subject subsequent to the first-mentioned measurement,
 (d) determining any difference between the first-mentioned and subsequent measurements, and
 (e) comparing said difference to a range of values of change of Hunter b to determine whether a change in Hunter b value inside or outside said range is present, indicative of either the presence or absence of the condition.

27. The process according to any one of claims 4, 11, 13, 22, 25 or 26 wherein step (a) comprises measuring the value of a color factor that is further dependent on lightness of the coloration of the test subject.

28. The process according to any one of claims 4, or 26 wherein step (a) comprises measuring a value of color factor Hunter b and wherein, in step (b), the range of values is a range of Hunter b values.

29. A process of detecting a condition in a test subject, which condition includes a symptomatic, detectable change in the test subject's coloration, the process comprising the steps of:
  (a) at a first point in time, measuring with a color measuring instrument a value of at least one color factor in the test subject's coloration, said color factor being dependent, at least in part, on relative content of one or more colors in said coloration,
  (b) waiting an interval,
  (c) measuring with the color measuring instrument, at least at one further point in time, a value of said color factor in the test subject's coloration, and
  (d) comparing the values of said color factor measured at said first and said further point in time to determine whether there has been established a change therein of a predetermined magnitude evidencing said condition, and
  wherein each of steps (a) and (c) comprises measuring the value of a color factor that is dependent on lightness of said coloration.

30. The process according to any one of claims 1, 2, 11, 12, 13, 22 or 29 wherein the color measuring instrument has a memory and a means for computation, wherein, prior to step (c), the process further comprises the step of storing in the memory the color factor value measured in step (a) and wherein step (d) comprises comparing by the means for computation the stored color factor value and the value of said color factor measured at said further point in time.

31. The process according to any one of claims 1, 2, 11, 12, 13, 22, 26 or 29 wherein each of steps (a) and (c) comprises making a set of multiple measurements of the color factor value and averaging each set of multiple measurements.

32. The process according to any one of claims 1, 2, 11, 12, 13, 22, 26 or 29 wherein each of steps (a) and (c) comprises measuring the value of said color factor at different locations on the test subject.

33. The process according to any one of claims 2, 4, 11, 13, 22 or 29 wherein step (a) comprises measuring the value of a color factor that is dependent on relative content of opponent colors in said coloration.

34. The process according to any one of claims 1, 2, 4, 11, 12, 13, 22, 25, 26 or 29 further comprising the step of establishing a plurality of coloration classes in each of which a preestablished magnitude of change in value of said color factor is indicative of said condition.

35. The process according to claim 34 wherein said coloration classes are determined by ranges of Hunter L values; said ranges of Hunter L values being bounded by at least one of the Hunter L values substantially as follows:

Hunter L=27, 30, 33, 36, 39, 42, 45, 48, 51, 54, 57, 60, 63, 66 and 69.

36. The process according to any one of claims 1, 2, 4, 11, 13, 22 or 29 wherein step (a) comprises measuring the value of a color factor that is dependent on relative content of blue and yellow in said coloration.

37. The process according to any one of claims 1, 2, 4, 11, 13, 22 or 29 wherein step (a) comprises measuring the value of a color factor that is dependent on relative content of green and red in said coloration.

38. The process according to any one of claims 1, 2, 4, 11, 13, 22 or 29 wherein step (a) comprises measuring the value of a color factor that is dependent on yellowness of the coloration of the test subject.

39. The process according to any one of claims 1, 2, 4, 11, 13, 22 or 29, wherein step (a) comprises measuring the value of color factor Hunter b.

40. The process according to any one of claims 1, 4, 11, 13, 22 or 29 wherein step (a) comprises measuring the value of a color factor that comprises a first function weighted in a first portion of the spectrum and a second function weighted in a second portion of the spectrum; the color factor being further dependent on lightness of the coloration of the test subject.

41. The process according to any one of claims 1, 2, 4, 11, 12, 13, 14, 22, 25, 26 or 29 further comprising the steps of: calibrating the color measuring instrument by providing a colored tile with color and spectral characteristics specific to the color factor value to be measured, measuring the coloration of the tile to produce measurement indications and adjusting the measurement indications of the instrument to correspond to preselected values when measuring the coloration of the tile.

42. The process according to any one of claims 4 or 29 wherein step (a) comprises measuring a value of color factor Hunter b, and prior to step (b), the process further comprises measuring a value of the color factor Hunter a, comparing the measured Hunter a value with a range of Hunter a values, and carrying out step (b) only if the measured Hunter a value lies within an acceptable range.

43. The process according to any one of claims 4, 25, 26 or 29 further comprising, prior to step (b), the step of establishing a range of values of the color factor characteristic of subjects without said condition.

44. In a process for detecting the condition of a test subject, which condition includes a symptomatic, detectable coloration; the improvement comprising the steps of:
  (a) compiling a group of lightness measure value ranges, and
  (b) associating with each lightness measure value range a value of a color factor for use in comparison with a measurement of the value of that color factor in the coloration of a test subject having a measured lightness within said range.

45. The process according to any one of claims 1, 2, 4, 9, 11, 12, 14, 22, 25, 26, 29, or 44 wherein said process of detecting a condition comprises a process for detecting a condition that causes jaundice in a human child or adult test subject.

46. The process according to any one of claims 1, 2, 4, 9, 11, 12, 14, 22, 25, 26, 29 or 44 wherein the coloration is skin coloration, and the condition is hyperbilirubinemia.

47. The process according to any one of claims 1, 2, 4, 9, 11, 12, 14, 22, 25, 26, 29 or 44 wherein the process of detecting a condition in a test subject comprises detecting a condition in a biological test subject.

48. The process according to claim 47 wherein the process of detecting a condition in a biological test subject comprises detecting a condition in a human or animal test subject.

49. The process according to claim 48 wherein the process of detecting a condition in a human or animal test subject comprises detecting a condition in a test subject that is a human infant.

50. The process according to claim 47 wherein the process of detecting a condition in a biological test subject comprises detecting a condition in a biological test subject that is selected from the group consisting of plants and soil.

51. The process according to claim 47 wherein the process of detecting a condition in a biological test subject comprises detecting a condition in a biological test subject selected from the group consisting of tissue, excretions, body fluids, hair, and teeth.

52. The process according to any one of claims 1, 2, 4, 9, 11, 12, 14, 22, 25, 26, 29 or 44 wherein said process of detecting a condition in a test subject comprises a process of detecting a condition selected from the group consisting of liver disorders, hypertension, and tuberculosis.

53. The process according to claim 44 wherein step (a) comprises assembling the group of lightness measure value ranges in machine-readable, tangible form, and step (b) comprises associating the color factor value with each lightness measure value range in said machine-readable, tangible form.

54. The process according to claim 53 wherein step (b) comprises associating a value of color factor Hunter b with each lightness measure value range.

55. The process according to claim 54 wherein step (a) comprises compiling a group of values of lightness measure Hunter L.

56. The process according to claim 44, wherein step (a) comprises compiling a group of lightness measure color factor values that are substantially those of color factor Hunter L and step (b) comprises associating a value of at least one further color factor whose value is substantially that of color factor Hunter a with each lightness measure color factor value range, the relationship between said lightness measure color factor value ranges and said associated color factor values being substantially as follows:

| Hunter L | Hunter a |
|---|---|
| 24 (or less) to 44 | 4 to 16 |
| 45 to 54 | 4 to 18 |
| 55 to 59 | 5 to 25 |
| 60 to 71 (or more) | 6 to 30. |

57. The process according to claim 44 wherein step (b) comprises associating with each lightness measure value range a value of a yellowness-dependent color factor.

58. The process according to claim 44 wherein the color factor is Hunter b and the lightness measure value ranges are ranges of Hunter L, the process further comprising the step of measuring by instrument a Hunter L value of the test subject's coloration.

59. The process according to either claim 5 or 44 wherein said ranges of values are determined by ranges of Hunter L values; said ranges of Hunter L values being bounded by at least one of the Hunter L values substantially as follows:

Hunter L=27, 30, 33, 36, 39, 42, 45, 48, 51, 54, 57, 60, 63, 66 and 69.

60. A process of detecting hyperbilirubinemia in a test subject based on skin coloration of said test subject; the process comprising the steps of:
(a) measuring with a color measuring instrument a value of a first color factor whose value is substantially that of Hunter b in said skin coloration of the test subject,
(b) measuring with a color measuring instrument a value of a second color factor whose value is substantially that of Hunter L in said skin coloration of the test subject; and (c) comparing the measured value of said first color factor with a range of acceptable values of said first color factor that are found in subjects in the absence of hyperbilirubinemia, said subjects having a skin coloration corresponding to the particular measured value of said second color factor in said test subject to determine if the measured value of said first color factor lies inside or outside the range, wherein said range of acceptable values is selected from ranges substantially as follows:

| No. | Hunter L | Hunter b |
|---|---|---|
| 1. | <27 | −5* |
| 2. | <27 | 6 |
| 3. | <27 | 7 |
| 4. | <27 | 8 |
| 5. | <27 | 9 |
| 6. | <27 | 10 |
| 7. | <27 | 11 |
| 8. | <27 | 12+** |
| 9. | 27 to <30 | −5 |
| 10. | 27 to <30 | 6 |
| 11. | 27 to <30 | 7 |
| 12. | 27 to <30 | 8 |
| 13. | 27 to <30 | 9 |
| 14. | 27 to <30 | 10 |
| 15. | 27 to <30 | 11 |
| 16. | 27 to <30 | 12+ |
| 17. | 30 to <33 | −5 |
| 18. | 30 to <33 | 6 |
| 19. | 30 to <33 | 7 |
| 20. | 30 to <33 | 8 |
| 21. | 30 to <33 | 9 |
| 22. | 30 to <33 | 10 |
| 23. | 30 to <33 | 11 |
| 24. | 30 to <33 | 12+ |
| 25. | 33 to <36 | −5 |
| 26. | 33 to <36 | 6 |
| 27. | 33 to <36 | 7 |
| 28. | 33 to <36 | 8 |
| 29. | 33 to <36 | 9 |
| 30. | 33 to <36 | 10 |
| 31. | 33 to <36 | 11 |
| 32. | 33 to <36 | 12+ |
| 33. | 36 to <39 | −5 |
| 34. | 36 to <39 | 6 |
| 35. | 36 to <39 | 7 |
| 36. | 36 to <39 | 8 |
| 37. | 36 to <39 | 9 |
| 38. | 36 to <39 | 10 |
| 39. | 36 to <39 | 11 |
| 40. | 36 to <39 | 12 |
| 41. | 36 to <39 | 13 |
| 42. | 36 to <39 | 14 |
| 43. | 36 to <39 | 15+ |
| 44. | 39 to <42 | −5 |
| 45. | 39 to <42 | 6 |
| 46. | 39 to <42 | 7 |
| 47. | 39 to <42 | 8 |
| 48. | 39 to <42 | 9 |
| 49. | 39 to <42 | 10 |
| 50. | 39 to <42 | 11 |
| 51. | 39 to <42 | 12 |
| 52. | 39 to <42 | 13 |
| 53. | 39 to <42 | 14 |
| 54. | 39 to <42 | 15+ |
| 55. | 42 to <45 | −5 |
| 56. | 42 to <45 | 6 |
| 57. | 42 to <45 | 7 |
| 58. | 42 to <45 | 8 |
| 59. | 42 to <45 | 9 |
| 60. | 42 to <45 | 10 |
| 61. | 42 to <45 | 11 |
| 62. | 42 to <45 | 12 |
| 63. | 42 to <45 | 13 |
| 64. | 42 to <45 | 14 |
| 65. | 42 to <45 | 15 |
| 66. | 42 to <45 | 16 |

-continued

| No. | Hunter L | Hunter b |
|---|---|---|
| 67. | 42 to <45 | 17 |
| 68. | 42 to <45 | 18+ |
| 69. | 45 to <48 | −5 |
| 70. | 45 to <48 | 6 |
| 71. | 45 to <48 | 7 |
| 72. | 45 to <48 | 8 |
| 73. | 45 to <48 | 9 |
| 74. | 45 to <48 | 10 |
| 75. | 45 to <48 | 11 |
| 76. | 45 to <48 | 12 |
| 77. | 45 to <48 | 13 |
| 78. | 45 to <48 | 14 |
| 79. | 45 to <48 | 15 |
| 80. | 45 to <48 | 16 |
| 81. | 45 to <48 | 17 |
| 82. | 45 to <48 | 18+ |
| 83. | 48 to <51 | −5 |
| 84. | 48 to <51 | 6 |
| 85. | 48 to <51 | 7 |
| 86. | 48 to <51 | 8 |
| 87. | 48 to <51 | 9 |
| 88. | 48 to <51 | 10 |
| 89. | 48 to <51 | 11 |
| 90. | 48 to <51 | 12 |
| 91. | 48 to <51 | 13 |
| 92. | 48 to <51 | 14 |
| 93. | 48 to <51 | 15 |
| 94. | 48 to <51 | 16 |
| 95. | 48 to <51 | 17 |
| 96. | 48 to <51 | 18 |
| 97. | 48 to <51 | 19 |
| 98. | 48 to <51 | 20+ |
| 99. | 51 to <54 | −5 |
| 100. | 51 to <54 | 6 |
| 101. | 51 to <54 | 7 |
| 102. | 51 to <54 | 8 |
| 103. | 51 to <54 | 9 |
| 104. | 51 to <54 | 10 |
| 105. | 51 to <54 | 11 |
| 106. | 51 to <54 | 12 |
| 107. | 51 to <54 | 13 |
| 108. | 51 to <54 | 14 |
| 109. | 51 to <54 | 15 |
| 110. | 51 to <54 | 16 |
| 111. | 51 to <54 | 17 |
| 112. | 51 to <54 | 18 |
| 113. | 51 to <54 | 19 |
| 114. | 51 to <54 | 20+ |
| 115. | 54 to <57 | −5 |
| 116. | 54 to <57 | 6 |
| 117. | 54 to <57 | 7 |
| 118. | 54 to <57 | 8 |
| 119. | 54 to <57 | 9 |
| 120. | 54 to <57 | 10 |
| 121. | 54 to <57 | 11 |
| 122. | 54 to <57 | 12 |
| 123. | 54 to <57 | 13 |
| 124. | 54 to <57 | 14 |
| 125. | 54 to <57 | 15 |
| 126. | 54 to <57 | 16 |
| 127. | 54 to <57 | 17 |
| 128. | 54 to <57 | 18 |
| 129. | 54 to <57 | 19 |
| 130. | 54 to <57 | 20+ |
| 131. | 57 to <60 | −5 |
| 132. | 57 to <60 | 6 |
| 133. | 57 to <60 | 7 |
| 134. | 57 to <60 | 8 |
| 135. | 57 to <60 | 9 |
| 136. | 57 to <60 | 10 |
| 137. | 57 to <60 | 11 |
| 138. | 57 to <60 | 12 |
| 139. | 57 to <60 | 13 |
| 140. | 57 to <60 | 14 |
| 141. | 57 to <60 | 15 |
| 142. | 57 to <60 | 16 |
| 143. | 57 to <60 | 17 |
| 144. | 57 to <60 | 18 |
| 145. | 57 to <60 | 19 |
| 146. | 57 to <60 | 20+ |
| 147. | 60 to <63 | −5 |
| 148. | 60 to <63 | 6 |
| 149. | 60 to <63 | 7 |
| 150. | 60 to <63 | 8 |
| 151. | 60 to <63 | 9 |
| 152. | 60 to <63 | 10 |
| 153. | 60 to <63 | 11 |
| 154. | 60 to <63 | 12 |
| 155. | 60 to <63 | 13 |
| 156. | 60 to <63 | 14 |
| 157. | 60 to <63 | 15 |
| 158. | 60 to <63 | 16 |
| 159. | 60 to <63 | 17 |
| 160. | 60 to <63 | 18 |
| 161. | 60 to <63 | 19 |
| 162. | 60 to <63 | 20+ |
| 163. | 63 to <66 | −5 |
| 164. | 63 to <66 | 6 |
| 165. | 63 to <66 | 7 |
| 166. | 63 to <66 | 8 |
| 167. | 63 to <66 | 9 |
| 168. | 63 to <66 | 10 |
| 169. | 63 to <66 | 11 |
| 170. | 63 to <66 | 12 |
| 171. | 63 to <66 | 13 |
| 172. | 63 to <66 | 14 |
| 173. | 63 to <66 | 15 |
| 174. | 63 to <66 | 16 |
| 175. | 63 to <66 | 17 |
| 176. | 63 to <66 | 18 |
| 177. | 63 to <66 | 19 |
| 178. | 63 to <66 | 20+ |
| 179. | 66 to <69 | −5 |
| 180. | 66 to <69 | 6 |
| 181. | 66 to <69 | 7 |
| 182. | 66 to <69 | 8 |
| 183. | 66 to <69 | 9 |
| 184. | 66 to <69 | 10 |
| 185. | 66 to <69 | 11 |
| 186. | 66 to <69 | 12 |
| 187. | 66 to <69 | 13 |
| 188. | 66 to <69 | 14 |
| 189. | 66 to <69 | 15 |
| 190. | 66 to <69 | 16 |
| 191. | 66 to <69 | 17 |
| 192. | 66 to <69 | 18 |
| 193. | 66 to <69 | 19 |
| 194. | 66 to <69 | 20+ |
| 195. | ≧69 | −5 |
| 196. | ≧69 | 6 |
| 197. | ≧69 | 7 |
| 198. | ≧69 | 8 |
| 199. | ≧69 | 9 |
| 200. | ≧69 | 10 |
| 201. | ≧69 | 11 |
| 202. | ≧69 | 12 |
| 203. | ≧69 | 13 |
| 204. | ≧69 | 14 |
| 205. | ≧69 | 15 |
| 206. | ≧69 | 16 |
| 207. | ≧69 | 17 |
| 208. | ≧69 | 18 |
| 209. | ≧69 | 19 |
| 210. | ≧69 | 20+ |

Wherein the designation −5 means less than 5 but more than 4 and the designation +12 means more than 12 but less than 13.

61. In a process for determining a color characteristic, the improvement comprising the steps of:

(a) compiling a group of lightness measure color factor value ranges, said lightness measure color factor comprising a color factor whose value is substantially that of color factor Hunter L, and (b) associating with each lightness measure color factor value range a value of at least one further color factor for use in comparison with a measurement of the value of that color factor in the coloration of a test subject having a lightness measure color factor value in said range, said at least one further color factor comprising a color factor whose value is substantially that of color factor Hunter b and the relationship between said lightness measure color factor value ranges and said associated color factor values being substantially as follows:

| No. | Hunter L | Hunter b |
|---|---|---|
| 1. | <27 | −5* |
| 2. | <27 | 6 |
| 3. | <27 | 7 |
| 4. | <27 | 8 |
| 5. | <27 | 9 |
| 6. | <27 | 10 |
| 7. | <27 | 11 |
| 8. | <27 | 12+** |
| 9. | 27 to <30 | −5 |
| 10. | 27 to <30 | 6 |
| 11. | 27 to <30 | 7 |
| 12. | 27 to <30 | 8 |
| 13. | 27 to <30 | 9 |
| 14. | 27 to <30 | 10 |
| 15. | 27 to <30 | 11 |
| 16. | 27 to <30 | 12+ |
| 17. | 30 to <33 | −5 |
| 18. | 30 to <33 | 6 |
| 19. | 30 to <33 | 7 |
| 20. | 30 to <33 | 8 |
| 21. | 30 to <33 | 9 |
| 22. | 30 to <33 | 10 |
| 23. | 30 to <33 | 11 |
| 24. | 30 to <33 | 12+ |
| 25. | 33 to <36 | −5 |
| 26. | 33 to <36 | 6 |
| 27. | 33 to <36 | 7 |
| 28. | 33 to <36 | 8 |
| 29. | 33 to <36 | 9 |
| 30. | 33 to <36 | 10 |
| 31. | 33 to <36 | 11 |
| 32. | 33 to <36 | 12+ |
| 33. | 36 to <39 | −5 |
| 34. | 36 to <39 | 6 |
| 35. | 36 to <39 | 7 |
| 36. | 36 to <39 | 8 |
| 37. | 36 to <39 | 9 |
| 38. | 36 to <39 | 10 |
| 39. | 36 to <39 | 11 |
| 40. | 36 to <39 | 12 |
| 41. | 36 to <39 | 13 |
| 42. | 36 to <39 | 14 |
| 43. | 36 to <39 | 15+ |
| 44. | 39 to <42 | −5 |
| 45. | 39 to <42 | 6 |
| 46. | 39 to <42 | 7 |
| 47. | 39 to <42 | 8 |
| 48. | 39 to <42 | 9 |
| 49. | 39 to <42 | 10 |
| 50. | 39 to <42 | 11 |
| 51. | 39 to <42 | 12 |
| 52. | 39 to <42 | 13 |
| 53. | 39 to <42 | 14 |
| 54. | 39 to <42 | 15+ |
| 55. | 42 to <45 | −5 |
| 56. | 42 to <45 | 6 |
| 57. | 42 to <45 | 7 |
| 58. | 42 to <45 | 8 |
| 59. | 42 to <45 | 9 |
| 60. | 42 to <45 | 10 |
| 61. | 42 to <45 | 11 |
| 62. | 42 to <45 | 12 |
| 63. | 42 to <45 | 13 |
| 64. | 42 to <45 | 14 |
| 65. | 42 to <45 | 15 |
| 66. | 42 to <45 | 16 |
| 67. | 42 to <45 | 17 |
| 68. | 42 to <45 | 18+ |
| 69. | 45 to <48 | −5 |
| 70. | 45 to <48 | 6 |
| 71. | 45 to <48 | 7 |
| 72. | 45 to <48 | 8 |
| 73. | 45 to <48 | 9 |
| 74. | 45 to <48 | 10 |
| 75. | 45 to <48 | 11 |
| 76. | 45 to <48 | 12 |
| 77. | 45 to <48 | 13 |
| 78. | 45 to <48 | 14 |
| 79. | 45 to <48 | 15 |
| 80. | 45 to <48 | 16 |
| 81. | 45 to <48 | 17 |
| 82. | 45 to <48 | 18+ |
| 83. | 48 to <51 | −5 |
| 84. | 48 to <51 | 6 |
| 85. | 48 to <51 | 7 |
| 86. | 48 to <51 | 8 |
| 87. | 48 to <51 | 9 |
| 88. | 48 to <51 | 10 |
| 89. | 48 to <51 | 11 |
| 90. | 48 to <51 | 12 |
| 91. | 48 to <51 | 13 |
| 92. | 48 to <51 | 14 |
| 93. | 48 to <51 | 15 |
| 94. | 48 to <51 | 16 |
| 95. | 48 to <51 | 17 |
| 96. | 48 to <51 | 18 |
| 97. | 48 to <51 | 19 |
| 98. | 48 to <51 | 20+ |
| 99. | 51 to <54 | −5 |
| 100. | 51 to <54 | 6 |
| 101. | 51 to <54 | 7 |
| 102. | 51 to <54 | 8 |
| 103. | 51 to <54 | 9 |
| 104. | 51 to <54 | 10 |
| 105. | 51 to <54 | 11 |
| 106. | 51 to <54 | 12 |
| 107. | 51 to <54 | 13 |
| 108. | 51 to <54 | 14 |
| 109. | 51 to <54 | 15 |
| 110. | 51 to <54 | 16 |
| 111. | 51 to <54 | 17 |
| 112. | 51 to <54 | 18 |
| 113. | 51 to <54 | 19 |
| 114. | 51 to <54 | 20+ |
| 115. | 54 to <57 | −5 |
| 116. | 54 to <57 | 6 |
| 117. | 54 to <57 | 7 |
| 118. | 54 to <57 | 8 |
| 119. | 54 to <57 | 9 |
| 120. | 54 to <57 | 10 |
| 121. | 54 to <57 | 11 |
| 122. | 54 to <57 | 12 |
| 123. | 54 to <57 | 13 |
| 124. | 54 to <57 | 14 |
| 125. | 54 to <57 | 15 |
| 126. | 54 to <57 | 16 |
| 127. | 54 to <57 | 17 |
| 128. | 54 to <57 | 18 |
| 129. | 54 to <57 | 19 |
| 130. | 54 to <57 | 20+ |
| 131. | 57 to <60 | −5 |
| 132. | 57 to <60 | 6 |
| 133. | 57 to <60 | 7 |
| 134. | 57 to <60 | 8 |
| 135. | 57 to <60 | 9 |
| 136. | 57 to <60 | 10 |
| 137. | 57 to <60 | 11 |
| 138. | 57 to <60 | 12 |
| 139. | 57 to <60 | 13 |
| 140. | 57 to <60 | 14 |
| 141. | 57 to <60 | 15 |
| 142. | 57 to <60 | 16 |

-continued

| No. | Hunter L | Hunter b |
|---|---|---|
| 143. | 57 to <60 | 17 |
| 144. | 57 to <60 | 18 |
| 145. | 57 to <60 | 19 |
| 146. | 57 to <60 | 20+ |
| 147. | 60 to <63 | −5 |
| 148. | 60 to <63 | 6 |
| 149. | 60 to <63 | 7 |
| 150. | 60 to <63 | 8 |
| 151. | 60 to <63 | 9 |
| 152. | 60 to <63 | 10 |
| 153. | 60 to <63 | 11 |
| 154. | 60 to <63 | 12 |
| 155. | 60 to <63 | 13 |
| 156. | 60 to <63 | 14 |
| 157. | 60 to <63 | 15 |
| 158. | 60 to <63 | 16 |
| 159. | 60 to <63 | 17 |
| 160. | 60 to <63 | 18 |
| 161. | 60 to <63 | 19 |
| 162. | 60 to <63 | 20+ |
| 163. | 63 to <66 | −5 |
| 164. | 63 to <66 | 6 |
| 165. | 63 to <66 | 7 |
| 166. | 63 to <66 | 8 |
| 167. | 63 to <66 | 9 |
| 168. | 63 to <66 | 10 |
| 169. | 63 to <66 | 11 |
| 170. | 63 to <66 | 12 |
| 171. | 63 to <66 | 13 |
| 172. | 63 to <66 | 14 |
| 173. | 63 to <66 | 15 |
| 174. | 63 to <66 | 16 |
| 175. | 63 to <66 | 17 |
| 176. | 63 to <66 | 18 |
| 177. | 63 to <66 | 19 |
| 178. | 63 to <66 | 20+ |
| 179. | 66 to <69 | −5 |
| 180. | 66 to <69 | 6 |
| 181. | 66 to <69 | 7 |
| 182. | 66 to <69 | 8 |
| 183. | 66 to <69 | 9 |
| 184. | 66 to <69 | 10 |
| 185. | 66 to <69 | 11 |
| 186. | 66 to <69 | 12 |
| 187. | 66 to <69 | 13 |
| 188. | 66 to <69 | 14 |
| 189. | 66 to <69 | 15 |
| 190. | 66 to <69 | 16 |
| 191. | 66 to <69 | 17 |
| 192. | 66 to <69 | 18 |
| 193. | 66 to <69 | 19 |
| 194. | 66 to <69 | 20+ |
| 195. | ≧69 | −5 |
| 196. | ≧69 | 6 |
| 197. | ≧69 | 7 |
| 198. | ≧69 | 8 |
| 199. | ≧69 | 9 |
| 200. | ≧69 | 10 |
| 201. | ≧69 | 11 |
| 202. | ≧69 | 12 |
| 203. | ≧69 | 13 |
| 204. | ≧69 | 14 |
| 205. | ≧69 | 15 |
| 206. | ≧69 | 16 |
| 207. | ≧69 | 17 |
| 208. | ≧69 | 18 |
| 209. | ≧69 | 19 |
| 210. | ≧69 | 20+ |

Wherein the designation −5 means less than 5 but more than 4 and the designation +12 means more than 12 but less than 13.

62. The process according to claim 61 wherein the process for determining a color characteristic comprises a process for determining a color characteristic in a biological test subject.

63. The process according to claim 61 wherein the process for determining a color characteristic comprises a process for determining a color characteristic in a biological test subject that is a human or animal test subject.

64. In a process for determining a color characteristic, the improvement comprising the steps of:
   (a) compiling a group of lightness measure color factor value ranges, said lightness measure color factor comprising a color factor whose value is substantially that of Hunter L, and
   (b) associating with each lightness measure color factor value range a value of at least one further color factor for use in comparison with a measurement of the value of that at least one further color factor in the coloration of a test subject having a lightness measure color factor value in a corresponding range, said at least one further color factor comprising a color factor whose value is substantially that of color factor Hunter a, and the relationship between said lightness measure color factor value ranges and said associated color factor values being substantially as follows:

| Hunter L | Hunter a |
|---|---|
| 24 (or less) to 44 | 4 to 16 |
| 45 to 54 | 4 to 18 |
| 55 to 59 | 5 to 25 |
| 60 to 71 (or more) | 6 to 30. |

65. In a process for determining a color characteristic, the improvement comprising the steps of:
   (a) compiling a group of lightness measure color factor value ranges, said ranges comprising at least one range of a color factor whose value is substantially that of color factor Hunter L, said at least one range being selected from the ranges substantially as follows:

Hunter L=<27, 27 to <30, 30 to <33, 33 to <36, 36 to <39, 39 to <42, 42 to <45, 45 to <48, 48 to <51, 51 to <54, 54 to <57, 57 to <60, 60 to <63, 63 to <66, 66 to <69, and ≦69, and (b) associating with each lightness measure color factor value range a value of a color factor for use in comparison with a measurement of the value of that color factor in the coloration of a test subject having a lightness measure color factor value within said range.

66. A process of evaluating a test subject based on the coloration of said test subject, the process comprising the steps of:
   (a) measuring with a color measuring instrument a value of a first color factor in said test subject's coloration, said first color factor being dependent on the lightness of the coloration of said test subject; and
   (b) measuring with a color measuring instrument a value of at least one further color factor in said test subject's coloration, said further color factor being dependent on the relative content of opponent colors in the coloration of said test subject;
   wherein at least one of steps (a) and (b) comprises arriving at a value of said color factor that correlates to a measure of coloration having established laboratory utility.

67. The process according to claim 66, further comprising the step of comparing the measured values of said first color factor and said at least one further color factor with a range of values of said color factors that are found in the colorations of subjects other than said test subject, to determine where within said range the measured values of said color factors lie.

68. The process according to either of claims 66 or 67, wherein the test subject is selected from the group consisting of skin, tissue, excretions, bodily fluids, hair and teeth.

69. The process according to either of claims 66 or 67, wherein step (b) comprises measuring the value of at least one further color factor that is dependent on relative content of blue and yellow in said coloration.

70. The process according to either of claims 66 or 67, wherein step (b) comprises measuring the value of at least one further color factor that is dependent on relative content of red and green in said coloration.

71. The process according to either of claims 66 or 67, wherein each of steps (a) and (b) comprises measuring the values of said first color factor and said at least one further color factor at different locations on the test subject.

72. The process according to either of claims 66 or 67, wherein each of steps (a) and (b) comprises making a set of multiple measurements of the values of each of said first color factor and said at least one further color factor and averaging each set of multiple measurements.

73. In a process for evaluating the coloration of a test subject, the improvement comprising the steps of:

(a) compiling a group of lightness measure color factor value ranges, said lightness measure color factor comprising a color factor whose value is substantially that of color factor Hunter L; and (b) associating with each lightness measure color factor value range a value of at least one further color factor for use in comparison with a measurement of the value of that color factor in the coloration of a test subject having a lightness measure color value in said range, said at least one further color factor comprising a color factor whose value is substantially that of at least one of color factors Hunter b and Hunter a, and the relationship between said lightness measure color factor value ranges and said associated color factor values being substantially as follows:

| CATEGORY NAME | L Min | L Max | a Min | a Max | b Min | b Max |
|---|---|---|---|---|---|---|
| Black | 0.00 | 14.00 | −10.00 | 3.00 | −10.00 | 5.00 |
| Darkest Dark Brown | 14.00 | 16.00 | −10.00 | 3.00 | −10.00 | 1.00 |
| Darkest Dark Brown | 14.00 | 16.00 | −10.00 | 3.00 | 1.00 | 1.15 |
| Darkest Dark Brown | 14.00 | 16.00 | −10.00 | 3.00 | 1.15 | 1.25 |
| Darkest Dark Brown | 14.00 | 16.00 | −10.00 | 3.00 | 1.25 | 3.00 |
| Darker Dark Brown | 16.00 | 19.00 | −10.00 | 3.00 | −10.00 | 2.70 |
| Darker Dark Brown | 16.00 | 19.00 | −10.00 | 3.00 | 2.70 | 2.95 |
| Darker Dark Brown | 16.00 | 19.00 | −10.00 | 3.00 | 2.95 | 3.20 |
| Darker Dark Brown | 16.00 | 19.00 | −10.00 | 3.00 | 3.20 | 10.00 |
| Darker Dark Brown (Cool Auburn Tones) | 16.00 | 19.00 | 2.00 | 3.00 | −10.00 | 2.70 |
| Darker Dark Brown (Warm Auburn Tones) | 16.00 | 19.00 | 2.00 | 3.00 | 3.20 | 10.00 |
| Brown | 19.00 | 22.00 | 0.00 | 6.00 | −10.00 | 2.95 |
| Brown | 19.00 | 22.00 | 0.00 | 6.00 | 2.95 | 3.20 |
| Brown | 19.00 | 22.00 | 0.00 | 6.00 | 3.20 | 3.45 |
| Brown | 19.00 | 22.00 | 0.00 | 6.00 | 3.45 | 10.00 |
| Brown (Warm Auburn Tones) | 19.00 | 22.00 | 3.50 | 6.00 | 3.45 | 10.00 |
| Brown (Cool Auburn Tones) | 19.00 | 22.00 | 3.50 | 6.00 | −10.00 | 3.45 |
| Medium Brown | 22.00 | 27.00 | 1.00 | 6.00 | −10.00 | 3.75 |
| Medium Brown | 22.00 | 27.00 | 1.00 | 6.00 | 3.75 | 4.00 |
| Golden Med. Brown | 22.00 | 27.00 | 1.00 | 6.00 | 4.00 | 4.25 |
| Golden Med. Brown | 22.00 | 27.00 | 1.00 | 6.00 | 4.25 | 10.00 |
| Medium Brown (Warm Auburn Tones) | 22.00 | 27.00 | 3.50 | 6.00 | 4.25 | 10.00 |
| Medium Brown (Cool Auburn Tones) | 22.00 | 27.00 | 3.50 | 6.00 | −10.00 | 4.25 |
| Darkest Med. Blonde | 27.00 | 28.00 | 1.80 | 6.00 | −5.00 | 6.00 |
| Darkest Med. Blonde | 27.00 | 28.00 | 1.80 | 5.00 | 6.00 | 6.50 |
| Darkest Med. Blonde | 27.00 | 28.00 | 5.00 | 6.00 | 6.00 | 6.50 |
| Darkest Med. Blonde | 27.00 | 28.00 | 1.80 | 6.00 | 6.50 | 15.00 |
| Medium Blonde | 28.00 | 31.00 | 1.80 | 6.00 | −5.00 | 6.00 |
| Medium Blonde | 28.00 | 31.00 | 1.80 | 5.00 | 6.00 | 6.50 |
| Med. Golden Blonde | 28.00 | 31.00 | 5.00 | 6.00 | 6.00 | 6.50 |
| Med. Golden Blonde | 28.00 | 31.00 | 1.80 | 6.00 | 6.50 | 15.00 |
| Lightest Med. Blonde | 31.00 | 33.00 | 1.80 | 6.00 | −5.00 | 6.00 |
| Lightest Med. Blonde | 31.00 | 33.00 | 1.80 | 5.00 | 6.00 | 6.50 |
| Lightest Med. Blonde | 31.00 | 33.00 | 5.00 | 6.00 | 6.00 | 6.50 |
| Lightest Med. Blonde | 31.00 | 33.00 | 1.80 | 6.00 | 6.50 | 15.00 |
| Light Blonde | 33.00 | 36.00 | 1.80 | 6.00 | −5.00 | 7.00 |
| Light Blonde | 33.00 | 36.00 | 1.80 | 5.00 | 7.00 | 7.50 |
| Light Blonde | 33.00 | 36.00 | 5.00 | 6.00 | 7.00 | 7.50 |
| Light Blonde | 33.00 | 36.00 | 1.80 | 6.00 | 7.50 | 20.00 |
| Lighter Blonde | 36.00 | 40.00 | 1.80 | 6.00 | −5.00 | 8.00 |
| Lighter Blonde | 36.00 | 40.00 | 1.80 | 5.00 | 8.00 | 8.50 |
| Lighter Blonde | 36.00 | 40.00 | 5.00 | 6.00 | 8.00 | 8.50 |
| Lighter Blonde | 36.00 | 40.00 | 1.80 | 6.00 | 8.50 | 20.00 |
| Lightest Blonde | 40.00 | 80.00 | 1.80 | 7.00 | −5.00 | 9.00 |
| Lightest Blonde | 40.00 | 80.00 | 1.80 | 5.00 | 9.00 | 10.00 |
| Lightest Blonde | 40.00 | 80.00 | 5.00 | 7.00 | 9.00 | 10.00 |
| Lightest Blonde | 40.00 | 80.00 | 1.80 | 7.00 | 10.00 | 30.00 |
| Light Red | 22.00 | 28.00 | 6.00 | 30.00 | −5.00 | 3.50 |
| Light Red | 22.00 | 28.00 | 6.00 | 30.00 | 3.50 | 3.75 |
| Light Red | 22.00 | 28.00 | 6.00 | 30.00 | 3.75 | 4.00 |
| Light Red | 22.00 | 28.00 | 6.00 | 30.00 | 4.00 | 30.00 |
| Medium Red | 19.00 | 22.00 | 6.00 | 30.00 | −10.00 | 3.50 |
| Medium Red | 19.00 | 22.00 | 6.00 | 30.00 | 3.50 | 3.75 |
| Med. Golden Red | 19.00 | 22.00 | 6.00 | 30.00 | 3.75 | 4.00 |
| Med. Golden Red | 19.00 | 22.00 | 6.00 | 30.00 | 4.00 | 30.00 |
| Dark Red | 14.00 | 19.00 | 3.00 | 30.00 | −10.00 | 2.50 |
| Dark Red | 14.00 | 19.00 | 3.00 | 30.00 | 2.50 | 2.75 |
| Dark Red | 14.00 | 19.00 | 3.00 | 30.00 | 2.75 | 3.00 |
| Dark Red | 14.00 | 19.00 | 3.00 | 30.00 | 3.00 | 30.00 |
| Red Blonde | 27.00 | 40.00 | 6.00 | 30.00 | 6.00 | 30.00 |
| Red Blonde | 40.00 | 80.00 | 7.00 | 30.00 | 6.00 | 30.00 |

| CATEGORY NAME | L Min | L Max | a Min | a Max | b Min | b Max |
|---|---|---|---|---|---|---|
| Black/Dk Brown/Med Brown/Brown w/ 70%–90% Grey | 27.00 | 50.00 | −10.00 | 1.80 | −10.00 | 3.75 |
| Black/Dk Brown/Med Brown/Brown w/ 70%–90% Grey | 27.00 | 50.00 | −10.00 | 1.80 | 3.75 | 4.00 |
| Black/Dk Brown/Med Brown/Brown w/ 70%–90% Grey | 27.00 | 50.00 | −10.00 | 1.80 | 4.00 | 4.25 |
| Black/Dk Brown/Med Brown/Brown w/ 70%–90% Grey | 27.00 | 50.00 | −10.00 | 1.80 | 4.25 | 10.00 |
| Black/Dk Brown/Med Brown/Brown w/ 40%–60% Grey | 23.00 | 27.00 | −10.00 | 1.00 | −10.00 | 3.75 |
| Black/Dk Brown/Med Brown/Brown w/ 40%–60% Grey | 23.00 | 27.00 | −10.00 | 1.00 | 3.75 | 4.00 |
| Black/Dk Brown/Med Brown/Brown w/ 40%–60% Grey | 23.00 | 27.00 | −10.00 | 1.00 | 4.00 | 4.25 |
| Black/Dk Brown/Med Brown/Brown w/ 40%–6% Grey | 23.00 | 27.00 | −10.00 | 1.00 | 4.25 | 10.00 |
| For Grey Hair | | | | | | |
| Light Brown/Darkest Blonde | | | | | | |
| 40%–60% Grey | 4.00 | 10.00 | −10.00 | −0.08 | | |
| 70%–90% Grey | 10.00 | To Maximum | −10.00 | −0.08 | | |
| Dark Red, Medium Red or Medium Light Red | | | | | | |
| 40%–60% Grey | 6.00 | 10.00 | −10.00 | −0.80 | | |
| 70%–90% Grey | 10.00 | To Maximum | −10.00 | −0.80 | | |
| Light Red or Red Blonde | | | | | | |
| 40%–60% Grey | 5.00 | 7.00 | −10.00 | −0.80 | | |
| 70%–90% Grey | 7.00 | To Maximum | −10.00 | −0.80 | | |
| Medium to Medium Dark Blonde | | | | | | |
| 40%–60% Grey | 1.70 | 4.00 | 0.00 | 0.00 | | |
| 70%–90% Grey | 4.00 | To Maximum | 0.00 | 0.00 | | |
| Light Blonde Hair | | | | | | |
| 40%–60% Grey | −99.99 | −0.25 | −1.75 | −1.25 | | |
| 70%–90% Grey | −99.99 | −0.25 | −99.99 | −1.75 | | |

Wherein negative values denote values less than zero.

74. The process according to claim 73 wherein step (a) comprises assembling the group of lightness measure color factor value ranges in machine-readable, tangible form and step (b) comprises associating said at least one further color factor value with each lightness measure color factor value range in said machine-readable, tangible form.

* * * * *

UNITED STATES PATENT AND TRADEMARK OFFICE
CERTIFICATE OF CORRECTION

PATENT NO. : 5,671,735

DATED : September 30, 1997

INVENTOR(S) : Macfarlane et al.

It is certified that error appears in the above-identified patent and that said Letters Patent is hereby corrected as shown below:

Col. 7, line 25, "vales" should read --values--;
Col. 20, line 39, "east" should read --least--;
Col. 21, line 48 (No. 52), "-42" should read --<42--;
Col. 21, line 50 (No. 55), "-45" should read --<45--;
Col. 23, line 61, "48," should read --48, 51--.

Signed and Sealed this

Seventh Day of March, 2000

Attest:

Attesting Officer

Q. TODD DICKINSON

Commissioner of Patents and Trademarks